(12) United States Patent
Yamamoto

(10) Patent No.: US 10,516,836 B2
(45) Date of Patent: Dec. 24, 2019

(54) IMAGING DEVICE

(71) Applicant: OLYMPUS CORPORATION, Hachioji-shi, Tokyo (JP)

(72) Inventor: Yusuke Yamamoto, Kawasaki (JP)

(73) Assignee: OLYMPUS CORPORATION, Tokyo (JP)

(*) Notice: Subject to any disclaimer, the term of this patent is extended or adjusted under 35 U.S.C. 154(b) by 253 days.

(21) Appl. No.: 15/630,267

(22) Filed: Jun. 22, 2017

(65) Prior Publication Data

US 2017/0289467 A1    Oct. 5, 2017

Related U.S. Application Data

(63) Continuation of application No. PCT/JP2015/051639, filed on Jan. 22, 2015.

(51) Int. Cl.
*H04N 5/33* (2006.01)
*G01J 3/02* (2006.01)
(Continued)

(52) U.S. Cl.
CPC ............ *H04N 5/332* (2013.01); *A61B 1/043* (2013.01); *A61B 1/0638* (2013.01);
(Continued)

(58) Field of Classification Search
CPC ......... H01L 27/14647; H01L 27/14645; H01L 27/14621; H01L 27/14627;
(Continued)

(56) References Cited

U.S. PATENT DOCUMENTS

2010/0141748 A1* 6/2010 Yamaguchi .......... H04N 5/2354
348/68
2012/0268573 A1   10/2012 Schonborn et al.
(Continued)

FOREIGN PATENT DOCUMENTS

JP    10-201707 A    8/1998
JP    2002-560 A     1/2002
(Continued)

OTHER PUBLICATIONS

International Search Report dated Apr. 21, 2015, issued in counterpart International Application No. PCT/JP2015/051639, w/English translation (4 pages).
(Continued)

*Primary Examiner* — Hung Q Dang
(74) *Attorney, Agent, or Firm* — Westerman, Hattori, Daniels & Adrian, LLP

(57) ABSTRACT

An imaging device includes a light splitting unit which splits first light from a subject into second light and third light, first and second imaging units, and an arithmetic unit. The first light includes the second light having infrared light and at least one of green light and blue light, and the third light having red light or the green light. The first imaging unit includes a first and a second light reception regions. The first light reception region generates at least one of the group consisting of a B signal according to the blue light and a G signal according to the green light. The second light reception region generates an IR signal according to the infrared light. The arithmetic unit generates a visible light image signal from the R signal, the G signal, and the B signal and generates an infrared light image signal from the IR signal.

11 Claims, 17 Drawing Sheets

(51) Int. Cl.
  *G01J 3/51* (2006.01)
  *G01J 3/44* (2006.01)
  *G01J 3/28* (2006.01)
  *H04N 9/04* (2006.01)
  *A61B 1/04* (2006.01)
  *A61B 1/06* (2006.01)
  *G02B 5/20* (2006.01)
  *G02B 5/22* (2006.01)
  *G02B 27/10* (2006.01)
  *H01L 27/146* (2006.01)
  *H04N 5/225* (2006.01)
  *H04N 9/097* (2006.01)
  *G01N 21/64* (2006.01)

(52) U.S. Cl.
  CPC .......... *A61B 1/0646* (2013.01); *G01J 3/0205* (2013.01); *G01J 3/0218* (2013.01); *G01J 3/0227* (2013.01); *G01J 3/28* (2013.01); *G01J 3/2823* (2013.01); *G01J 3/4406* (2013.01); *G01J 3/51* (2013.01); *G01J 3/513* (2013.01); *G01N 21/64* (2013.01); *G02B 5/208* (2013.01); *G02B 5/223* (2013.01); *G02B 27/1013* (2013.01); *H01L 27/14621* (2013.01); *H04N 5/2256* (2013.01); *H04N 9/045* (2013.01); *H04N 9/097* (2013.01); *G01J 2003/2826* (2013.01); *H01L 27/14634* (2013.01); *H01L 27/14645* (2013.01); *H01L 27/14649* (2013.01); *H04N 2005/2255* (2013.01)

(58) Field of Classification Search
  CPC ............ H01L 27/14605; G02B 27/145; G02B 27/1086; G02B 27/1013; G02B 27/102; G02B 27/1046; G02B 27/141; G02B 26/008; H04N 9/045; H04N 9/3105; H04N 9/3164; H04N 9/3167; H04N 9/315; H04N 9/09; H04N 5/3696; H04N 9/097; G03B 33/12; G03B 21/2066; G03B 21/006; G03B 21/2033; G11B 7/1381
  See application file for complete search history.

(56) References Cited

U.S. PATENT DOCUMENTS

2014/0232912 A1* 8/2014 Morimoto .............. G03B 11/00
  348/270
2014/0320707 A1* 10/2014 Olson .................... H04N 5/332
  348/262

FOREIGN PATENT DOCUMENTS

| JP | 2002-16931 A | 1/2002 |
| JP | 2008-131292 A | 6/2008 |
| JP | 2011-528918 A | 12/2011 |
| WO | 2009/117483 A1 | 9/2009 |

OTHER PUBLICATIONS

Notice of Allowance dated Jul. 17, 2018 issued in counterpart Japanese application No. 2016-570413, with English translation. (6 pages).

* cited by examiner

| B | IR | B | IR | B | IR | B | — 3035a |
| IR | B | IR | B | IR | B | IR | — 3035b |
| B | IR | B | IR | B | IR | B | |
| IR | B | IR | B | IR | B | IR | |
| B | IR | B | IR | B | IR | B | |
| IR | B | IR | B | IR | B | IR | |

IMAGING DEVICE

This application is a continuation application based on a PCT International Application No. PCT/JP2015/051639, filed on Jan. 22, 2015. The content of the PCT International Application is incorporated herein by reference.

BACKGROUND OF THE INVENTION

Field of the Invention

The present invention relates to an imaging device.

Description of Related Art

An endoscope system capable of performing special light observation using infrared light in addition to normal observation using visible light is widely used. In the endoscope system, it is possible to treat a lesion found through normal observation or the special light observation with a treatment tool.

For example, in an endoscope system disclosed in Japanese Unexamined Patent Application, First Publication No. H10-201707, a fluorescent substance called indocyanine green (ICG) is irradiated with excitation light, and fluorescence from a lesion is detected. The ICG is administered to a body of a test target in advance. The ICG is excited in an infrared region by the excitation light and emits fluorescence. The administered ICG is accumulated into a lesion such as cancer. Since strong fluorescence is generated from the lesion, it is possible to determine the presence or absence of a lesion according to a captured fluorescence image.

In the endoscope system disclosed in Japanese Unexamined Patent Application, First Publication No. H10-201707, a subject is irradiated with light including visible light and infrared light. The infrared light includes excitation light. Light reflected by the subject and fluorescence (infrared fluorescence) generated from the subject are imaged via a dichroic mirror or a dichroic prism built into a camera head. Since a splitting means that performs splitting into the visible light and the fluorescence is provided, it is possible to simultaneously perform normal observation using the visible light and special light observation using the infrared light. Further, the fluorescence, the red light, the green light, and the blue light are imaged by respective different image sensors via the dichroic mirror or the dichroic prism. Therefore, it is possible to obtain a high-quality image.

FIG. 19 shows a configuration of an endoscope device 1001 that is the same as the configuration disclosed in Japanese Unexamined Patent Application, First Publication No. H10-201707. As shown in FIG. 19, the endoscope device 1001 includes a light source unit 1010, an endoscope scope unit 1020, a camera head 1030, a processor 1040, and a monitor 1050. In FIG. 19, a schematic configuration of the light source unit 1010, the endoscope scope unit 1020, and the camera head 1030 is shown.

The light source unit 1010 includes a light source 1100, a band pass filter 1101, and a condenser lens 1102. The light source 1100 emits light having wavelengths from a wavelength band of visible light to a wavelength band of infrared light. The wavelength band of the infrared light includes a wavelength band of excitation light and a wavelength band of fluorescence. The wavelength band of the fluorescence is a band in which a wavelength is longer than that in the wavelength band of the excitation light in the wavelength band of the infrared light. The band pass filter 1101 is provided on an illumination light path of the light source 1100. The band pass filter 1101 transmits only the visible light and the excitation light. The condenser lens 1102 condenses the light transmitted through the band pass filter 1101. A wavelength band of the infrared light emitted from the light source 1100 has only to include at least a wavelength band of the excitation light.

FIG. 20 shows transmission characteristics of the band pass filter 1101. A horizontal axis of a graph shown in FIG. 20 indicates wavelength, and the vertical axis indicates transmittance. The band pass filter 1101 transmits light in a wavelength band in which a wavelength is about 370 nm to about 800 nm. Further, the band pass filter 1101 filters out light in a wavelength band in which a wavelength is shorter than about 370 nm and light in a wavelength band in which a wavelength is equal to or longer than 800 nm. The wavelength band of light transmitted by the band pass filter 1101 includes a wavelength band of the visible light and a wavelength band of the excitation light. The wavelength band of the excitation light is a band in which the wavelength is about 750 nm to about 780 nm. The wavelength band of the light filtered out by the band pass filter 1101 includes a wavelength band of the fluorescence. The wavelength band of the fluorescence is a band in which the wavelength is equal to or longer than about 800 nm.

The endoscope scope unit 1020 includes a light guide 1200, an illumination lens 1201, an objective lens 1202, and an image guide 1203. The light from the light source 1100 is incident on the light guide 1200 via the band pass filter 1101 and the condenser lens 1102. The light guide 1200 transfers the light from the light source 1100 to a distal end portion of the endoscope scope unit 1020. A subject 1060 is irradiated with the light transferred by the light guide 1200, by the illumination lens 1201.

At the distal end portion of the endoscope scope unit 1020, the objective lens 1202 is provided adjacent to the illumination lens 1201. Light reflected by the subject 1060 and fluorescence generated from the subject 1060 are incident on the objective lens 1202. The light reflected by the subject 1060 includes visible light and excitation light. That is, light including the visible light, the excitation light, and the fluorescence is incident on the objective lens 1202. The objective lens 1202 images the light.

A distal end surface of the image guide 1203 is arranged at an image formation position of the objective lens 1202. The image guide 1203 transfers an optical image formed on the distal end surface to a proximal end surface.

The camera head 1030 includes an image formation lens 1300, a dichroic mirror 1301, an excitation light cut filter 1302, an image sensor 1303, a dichroic prism 1304, an image sensor 1305, an image sensor 1306, and an image sensor 1307. The image formation lens 1300 is arranged to face the proximal end surface of the image guide 1203. The image formation lens 1300 forms an optical image transferred by the image guide 1203 on the image sensor 1303, the image sensor 1305, the image sensor 1306, and the image sensor 1307.

The dichroic mirror 1301 is arranged on an optical path from the image formation lens 1300 to an image formation position of the image formation lens 1300. The light passing through the image formation lens 1300 is incident on the dichroic mirror 1301. The dichroic mirror 1301 transmits the visible light and reflects light other than visible light. FIG. 21 shows characteristics of reflection and transmission of the dichroic mirror 1301. A horizontal axis of a graph shown in FIG. 21 indicates wavelength, and a vertical axis indicates transmittance. The dichroic mirror 1301 transmits light in a wavelength band in which a wavelength is shorter than about 700 nm. Further, the dichroic mirror 1301 reflects light in a wavelength band in which a wavelength is equal to or longer than 700 nm. The wavelength band of the light transmitted by the dichroic mirror 1301 includes a wavelength band of the visible light. The wavelength band of the light reflected by the dichroic mirror 1301 includes a wavelength band of infrared light.

An optical image of a visible light component is formed at the image formation position of the light transmitted through the dichroic mirror 1301. On the other hand, an optical image of an infrared light component is formed at the image formation position of the light reflected by the dichroic mirror 1301.

The light reflected by the dichroic mirror 1301 is incident on the excitation light cut filter 1302. The light incident on the excitation light cut filter 1302 includes the infrared light. The infrared light includes excitation light and fluorescence. The excitation light cut filter 1302 filters out the excitation light, and transmits the fluorescence. FIG. 22 shows transmission characteristics of the excitation light cut filter 1302. A horizontal axis of a graph shown in FIG. 22 indicates wavelength, and a vertical axis indicates transmittance. The excitation light cut filter 1302 filters out the light in a wavelength band in which a wavelength is shorter than about 800 nm. Further, the excitation light cut filter 1302 transmits light in a wavelength band in which a wavelength is equal to or longer than about 800 nm. The wavelength band of the light filtered out by the excitation light cut filter 1302 includes the wavelength band of the excitation light. The wavelength band of the light transmitted by the excitation light cut filter 1302 includes the wavelength band of the fluorescence.

The fluorescence transmitted through the excitation light cut filter 1302 is incident on the image sensor 1303. The image sensor 1303 generates an IR signal according to the fluorescence.

FIG. 23 shows characteristics of ICG that is administered to the subject 1060. horizontal axis of a graph shown in FIG. 23 indicates wavelength, and a vertical axis indicates intensity. In FIG. 23, characteristics of the excitation light that excites ICG and characteristics of the fluorescence emitted from ICG are shown. A peak wavelength of the excitation light is about 770 nm, and a peak wavelength of the fluorescence is about 820 nm. Thus, when the subject 1060 is irradiated with the excitation light having a wavelength of about 750 nm to about 780 nm, the fluorescence having a wavelength of about 800 nm to about 850 nm is generated from the subject 1060. By detecting the fluorescence emitted from the subject 1060, it is possible to detect the presence or absence of cancer. As shown in FIG. 20, the band pass filter 1101 transmits the excitation light having a wavelength of about 750 nm to about 780 nm, and filters out the fluorescence having a wavelength of about 800 nm to about 850 nm. Further, as shown in FIG. 22, the excitation light cut filter 1302 filters out the excitation light having a wavelength of about 750 nm to about 780 nm. Therefore, the image sensor 1303 can detect only the fluorescence.

The light in the visible light band transmitted through the dichroic mirror 1301 is incident on the dichroic prism 1304. The dichroic prism 1304 splits the light in the visible light band into light (red light) in a red wavelength band, light (green light) in a green wavelength band, and light (blue light) in a blue wavelength band. The red light passing through the dichroic prism 1304 is incident on the image sensor 1305. The image sensor 1305 generates an R signal according to the red light. The green light passing through the dichroic prism 1304 is incident on the image sensor 1306. The image sensor 1306 generates a G signal according to the green light. The blue light passing through the dichroic prism 1304 is incident on the image sensor 1307. The image sensor 1307 generates a B signal according to the blue light.

The processor 1040 generates a visible light image signal from the R signal, the G signal, and the B signal, and generates a fluorescence image signal from the IR signal. The monitor 1050 displays a visible light image according to the visible light image signal, and a fluorescent image according to the fluorescence image signal. For example, the monitor 1050 displays the visible light image and the fluorescence image acquired at the same time, side by side. Alternatively, the monitor 1050 superimposes and displays the visible light image and the fluorescence image acquired at the same time.

SUMMARY OF THE INVENTION

According to a first aspect of the present invention, an imaging device includes a light splitting unit, a first imaging unit, a second imaging unit, and an arithmetic unit. The light splitting unit is configured to split first light from a subject into second light and third light. The first light includes the second light and the third light. The second light includes infrared light, and at least one of a group consisting of green light and blue light. The third light includes red light. The third light further includes the green light when the second light includes the blue light and does not include the green light. The third light further includes the blue light when the second light includes the green light and does not include the blue light. A wavelength of the infrared light is longer than a wavelength of the red light. The wavelength of the red light is longer than a wavelength of the green light. The wavelength of the green light is longer than a wavelength of the blue light. The first imaging unit includes a first light reception region and a second light reception region. The second light passing through the light splitting unit is incident on the first light reception region. The first light reception region is configured to generate at least one of the group consisting of a B signal according to the blue light and a G signal according to the green light. The infrared light transmitted through the first light reception region is incident on the second light reception region. The second light reception region is configured to generate an IR signal according to the infrared light. The second imaging unit is configured to generate an R signal according to the red light included in the third light passing through the light splitting unit. The second imaging unit is configured to generate the G signal when the third light passing through the light splitting unit includes the green light and does not include the blue light. The second imaging unit is configured to generate the B signal when the third light passing through the light splitting unit includes the blue light and does not include the green light. The arithmetic unit is configured to generate a visible light image signal from the R signal, the G signal, and the B signal and generates an infrared light image signal from the IR signal.

According to a second aspect of the present invention, in the first aspect, the second light passing through the light splitting unit may include the infrared light and one of the blue light and the green light. The light splitting unit may further split the third light into the red light and the green light when the third light includes the green light. The light splitting unit may further split the third light into the red light and the blue light when the third light includes the blue light. The second imaging unit may include a third imaging unit and a fourth imaging unit. The third imaging unit may be configured to generate the R signal according to the red light passing through the light splitting unit. The fourth imaging unit may be configured to generate the G signal according to the green light passing through the light splitting unit when the third light includes the green light. The fourth imaging unit may be configured to generate the B signal according to the blue light passing through the light splitting unit when the third light includes the blue light.

According to a third aspect of the present invention, in the first aspect, the imaging device may further include an excitation light cut filter arranged on an optical path from the subject to the light splitting unit. The infrared light included in the second light in the first light from the subject may include excitation light and fluorescence. A wavelength of the fluorescence may be longer than a wavelength of the excitation light. The first light from the subject may be incident on the excitation light cut filter. The excitation light cut filter may filter out the excitation light, and transmit the fluorescence, the red light, the green light, and the blue light. The light splitting unit may split the first light transmitted through the excitation light cut filter into the second light and the third light. The fluorescence transmitted through the first light reception region may be incident on the second light reception region. The second light reception region may be configured to generate the IR signal according to the fluorescence.

According to a fourth aspect of the present invention, in the third aspect, the second light reception region has a sensitivity to light which has a wavelength equal to or longer than a wavelength of a lower limit of a wavelength band that is capable of being filtered out by the excitation light cut filter.

According to a fifth aspect of the present invention, in the first aspect, the imaging device may further include an excitation light cut filter arranged on an optical path from the light splitting unit to the first imaging unit. The infrared light included in the second light in the first light from the subject may include excitation light and fluorescence. A wavelength of the fluorescence may be longer than a wavelength of the excitation light. The second light passing through the light splitting unit may be incident on the excitation light cut filter. The excitation light cut filter may filter out the excitation light, and transmit the fluorescence, and at least one of the group consisting of the green light and the blue light. The fluorescence transmitted through the first light reception region may be incident on the second light reception region. The second light reception region may be configured to generate the IR signal according to the fluorescence.

According to a sixth aspect of the present invention, in the fifth aspect, the excitation light cut filter may be arranged on a surface of the first light reception region of the first imaging unit.

According to a seventh aspect of the present invention, in the fifth aspect, the excitation light cut filter may include an organic material. The organic material may filter out the excitation light and transmit at least one of the group consisting of the green light and the blue light, and the fluorescence.

According to an eighth aspect of the present invention, in the first aspect, the first imaging unit may include a semiconductor substrate. The first light reception region and the second light reception region may be arranged on the semiconductor substrate. The first light reception region and the second light reception region may be stacked.

According to a ninth aspect of the present invention, in the first aspect, the first imaging unit may include a first semiconductor substrate and a second semiconductor substrate. The first semiconductor substrate and the second semiconductor substrate may be stacked. The first light reception region may be arranged on the first semiconductor substrate. The second light reception region may be arranged on the second semiconductor substrate.

According to a tenth aspect of the present invention, in the ninth aspect, the imaging device may further include an excitation light cut filter arranged on an optical path from the subject to the light splitting unit. The second light included in the first light from the subject may include the infrared light and the blue light. The infrared light may include excitation light and fluorescence. A wavelength of the fluorescence may be longer than a wavelength of the excitation light. The third light included in the first light from the subject may include the red light and the green light. The first light from the subject may be incident on the excitation light cut filter. The excitation light cut filter may filter out the excitation light, and transmit the fluorescence, the red light, the green light, and the blue light. The light splitting unit may split the first light transmitted through the excitation light cut filter into the second light and the third light. The first imaging unit may further include a blue light cut filter. The blue light cut filter may be arranged between the first semiconductor substrate and the second semiconductor substrate. The first semiconductor substrate, the blue light cut filter, and the second semiconductor substrate may be stacked. The first light reception region may be configured to generate the B signal according to the blue light. The fluorescence and the blue light transmitted through the first light reception region may be incident on the blue light cut filter. The blue light cut filter may filter out the blue light and transmit the fluorescence. The fluorescence transmitted through the blue light cut filter may be incident on the second light reception region. The second light reception region may be configured to generate the IR signal according to the fluorescence. The second imaging unit may be configured to generate the R signal according to the red light and the G signal according to the green light.

According to an eleventh aspect of the present invention, in the ninth aspect, the imaging device may further include an excitation light cut filter arranged on an optical path from the light splitting unit to the first imaging unit. The second light included in the first light from the subject may include the infrared light and the blue light. The infrared light may include excitation light and fluorescence. A wavelength of the fluorescence may be longer than a wavelength of the excitation light. The third light included in the first light from the subject may include the red light and the green light. The second light passing through the light splitting unit may be incident on the excitation light cut filter. The excitation light cut filter may filter out the excitation light, and transmit the fluorescence and the blue light. The first imaging unit may further include a blue light cut filter. The blue light cut filter may be arranged between the first semiconductor substrate and the second semiconductor substrate. The first semiconductor substrate, the blue light cut filter, and the second semiconductor substrate may be stacked. The first light reception region may be configured to generate the B signal according to the blue light. The fluorescence and the blue light transmitted through the first light reception region may be incident on the blue light cut filter. The blue light cut filter may filter out the blue light and transmit the fluorescence. The fluorescence transmitted through the blue light cut filter may be incident on the second light reception region. The second light reception region may be configured to generate the IR signal according to the fluorescence. The second imaging unit may be configured to generate the R signal according to the red light and the G signal according to the green light.

According to a twelfth aspect of the present invention, in the third or the fifth aspect, the second light included in the first light from the subject may include the infrared light and the blue light. The third light included in the first light from the subject may include the red light and the green light. The first light reception region may be configured to generate the B signal according to the blue light. The second imaging unit may be configured to generate the R signal according to the red light and the G signal according to the green light. The arithmetic unit may be configured to generate the B signal only according to the blue light by removing a component derived from the fluorescence from the B signal generated in the first light reception region, according to a sensitivity of the first light reception region to the fluorescence, a sensitivity of the second light reception region to the fluorescence, and the IR signal generated in the second light reception region.

BRIEF DESCRIPTION OF DRAWINGS

FIG. 11 is a reference diagram showing a pixel array of an image sensor of the second modification example in the first embodiment of the present invention.

DETAILED DESCRIPTION OF THE INTENTION

Embodiments of the present invention will be described with reference to the drawings. In each of the following embodiments, an endoscope device that is an example of an imaging device will be described. The present invention is applicable to a device, a system, a module, and the like having an imaging function.

(First Embodiment)

Figure 1:
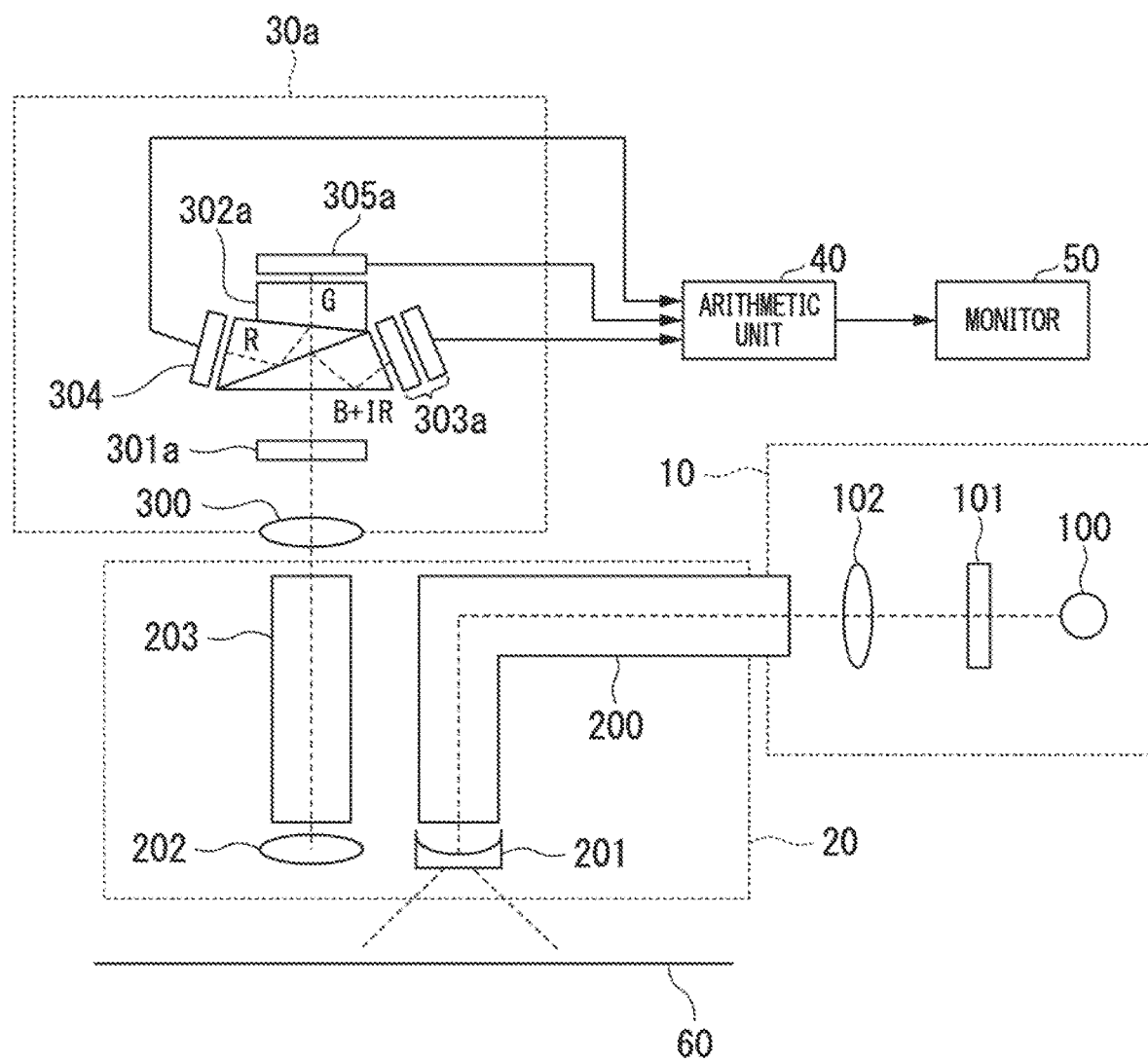
FIG. 1 is a block diagram showing a configuration of an endoscope device of a first embodiment of the present invention.

FIG. 1 shows a configuration of an endoscope device 1a of a first embodiment of the present invention. As shown in FIG. 1, an endoscope device 1a includes a light source unit 10, an endoscope scope unit 20, a camera head 30a, an arithmetic unit 40, and a monitor 50. In FIG. 1, a schematic configuration of the light source unit 10, the endoscope scope unit 20, and the camera head 30a is shown.

The light source unit 10 includes a light source 100, a band pass filter 101, and a condenser lens 102. The light source 100 emits light having a wavelength of a wavelength band of visible light to a wavelength band of infrared light. The wavelength band of the visible light includes a red wavelength band, a green wavelength band, and a blue wavelength band. The red wavelength band is a band including wavelengths longer than those of the green wavelength band. The green wavelength band is a band including wavelengths longer than those of the blue wavelength band. A wavelength band of the infrared light is a band including wavelengths longer than those of the red wavelength band. The wavelength band of the infrared light includes a wavelength band of excitation light and a wavelength band of fluorescence. The wavelength band of the fluorescence is a band including wavelengths longer than those of the wavelength band of the excitation light in the wavelength band of the infrared light. That is, the wavelength of the infrared light is longer than the wavelength of red light. The wavelength of the red light is longer than the wavelength of the green light. The wavelength of the green light is longer than the wavelength of the blue light. The wavelength band of the infrared light emitted by the light source 100 has only to include at least a wavelength band of the excitation light.

The band pass filter 101 is provided in an illumination light path of the light source 100. The band pass filter 101 transmits only the visible light and the excitation light. The condenser lens 102 condenses light transmitted through the band pass filter 101.

Figure 20:
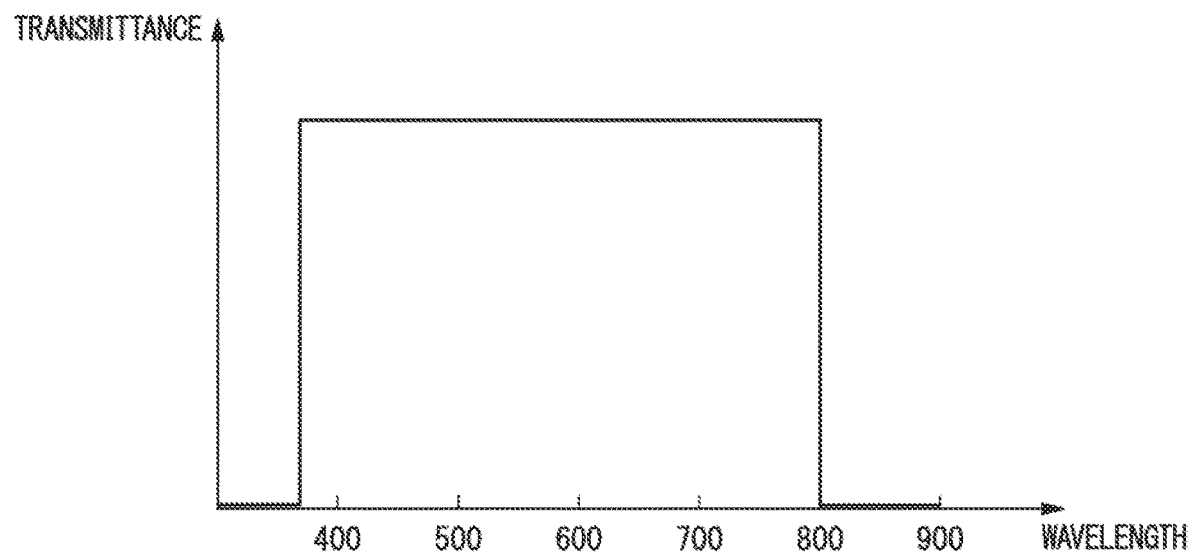
FIG. 20 is a graph showing characteristics of a band pass filter.
Figure 21:
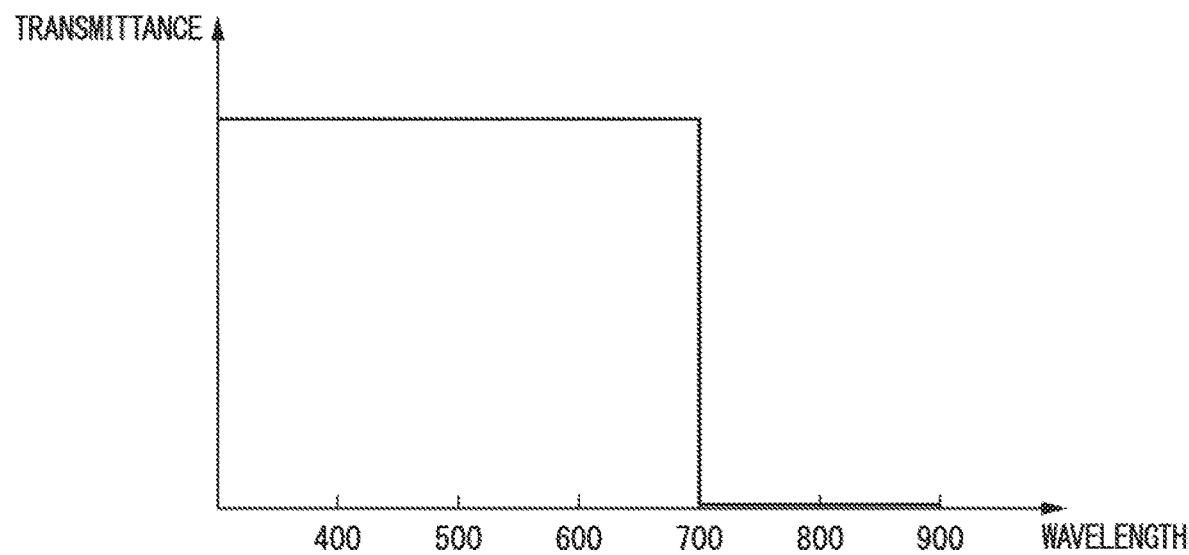
FIG. 21 is a graph showing characteristics of a dichroic mirror.
Figure 22:
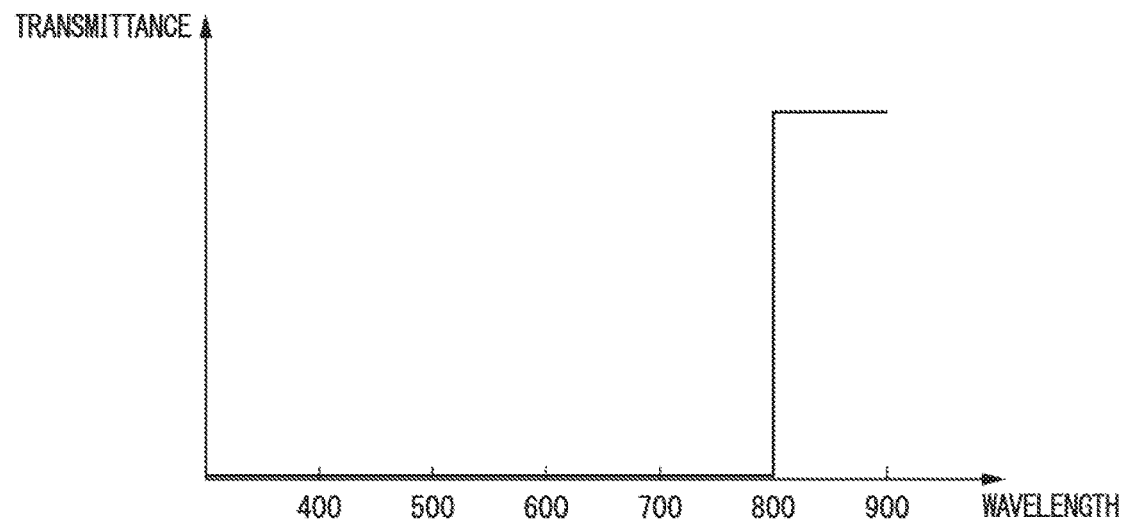
FIG. 22 is a graph showing characteristics of an excitation light cut filter.
Figure 23:
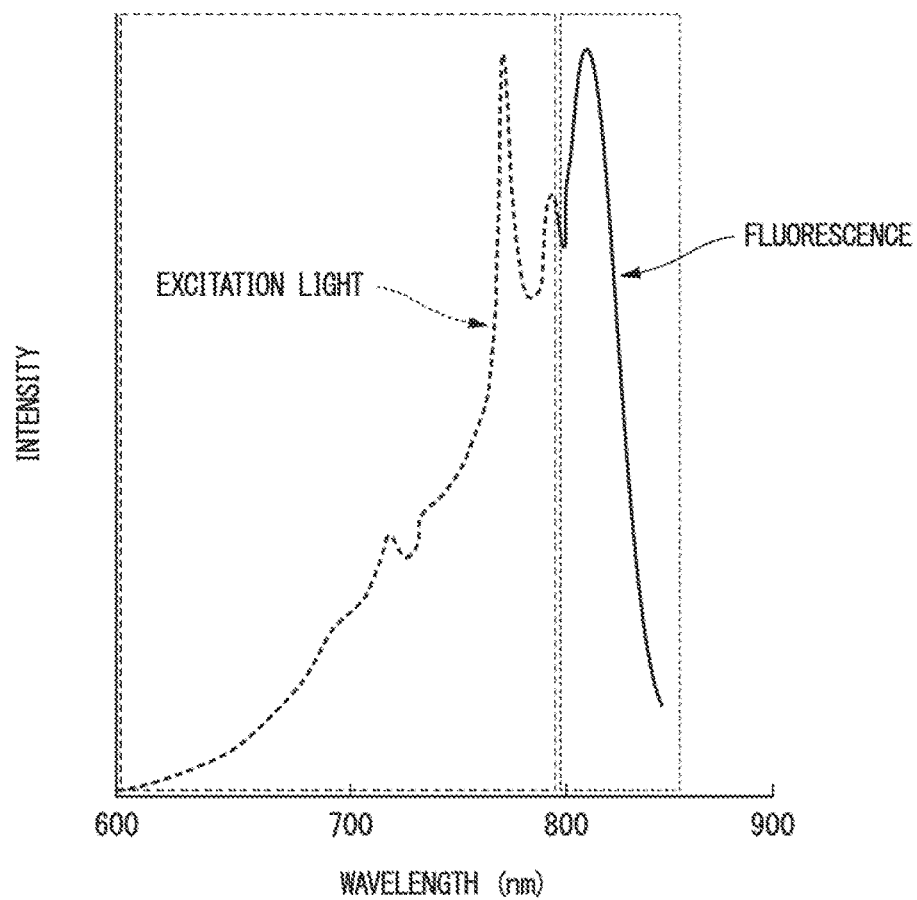
FIG. 23 is a graph showing characteristics of indocyanine green (ICG).

Transmission characteristics of the band pass filter 101 are the same as transmission characteristics shown in FIG. 20. The band pass filter 101 transmits light with a wavelength band in which a wavelength is about 370 nm to about 800 nm. The band pass filter 101 filters out light in a wavelength band in which the wavelength is shorter than about 370 nm and light in a wavelength band in which the wavelength is equal to or longer than about 800 nm. The wavelength band of the light transmitted by the band pass filter 101 includes a wavelength band of the visible light and a wavelength band of the excitation light. The wavelength band of the excitation light is a band in which a wavelength is about 750 nm to about 780 nm. A wavelength band of light filtered out by the band pass filter 101 includes the wavelength band of the fluorescence. The wavelength band of the fluorescence is a band in which a wavelength is about 800 nm to about 850 nm.

The endoscope scope unit 20 includes a light guide 200, an illumination lens 201, an objective lens 202, and an image guide 203. The light from the light source 100 is incident on the light guide 200 via the band pass filter 101 and the condenser lens 102. The light guide 200 sends the light from the light source 100 to a distal end portion of the endoscope scope unit 20. The subject 60 is irradiated with the light sent by the light guide 200, by the illumination lens 201.

At the distal end portion of the endoscope scope unit 20, the objective lens 202 is provided adjacent to the illumination lens 201. Light reflected by the subject 60 and fluorescence generated from the subject 60 are incident on the objective lens 202. The light reflected by the subject 60 includes visible light and excitation light. Light including the visible light, the excitation light, and the fluorescence is incident on the objective lens 202. The objective lens 202 forms an image of the light.

A distal end surface of the image guide 203 is arranged at an image formation position of the objective lens 202. The image guide 203 sends an optical image formed on the distal end surface to the proximal end surface.

The camera head 30a includes an image formation lens 300, an excitation light cut filter 301a, a dichroic prism 302a (a light splitting unit), an image sensor 303a (a first imaging unit), an image sensor 304 (a second imaging unit and a third imaging unit), and an image sensor 305a (a second imaging unit and a fourth imaging unit). The image formation lens 300 is arranged to face the proximal end surface of the image guide 203. The image formation lens 300 forms an optical image sent by the image guide 203 on the image sensor 303a, the image sensor 304, and the image sensor 305a.

The first light from the subject 60 includes second light and third light. The second light includes infrared light and blue light. The infrared light includes excitation light and fluorescence. A wavelength of the fluorescence is longer than a wavelength of the excitation light. The third light includes red light and green light.

The excitation light cut filter 301a is arranged on a light path from the image formation lens 300 to an image formation position of the image formation lens 300. The first light passing through the image formation lens 300, that is, the first light from the subject 60 is incident on the excitation light cut filter 301a. The excitation light cut filter 301a filters out the excitation light and transmits the fluorescence, the red light, the green light, and the blue light. The second light included in the first light passing through the excitation light cut filter 301a includes the fluorescence and the blue light. The third light included in the first light passing through the excitation light cut filter 301a includes the red light and the green light. The excitation light cut filter 301a has only to be arranged on an optical path from the subject 60 to the dichroic prism 302a.

Figure 2:
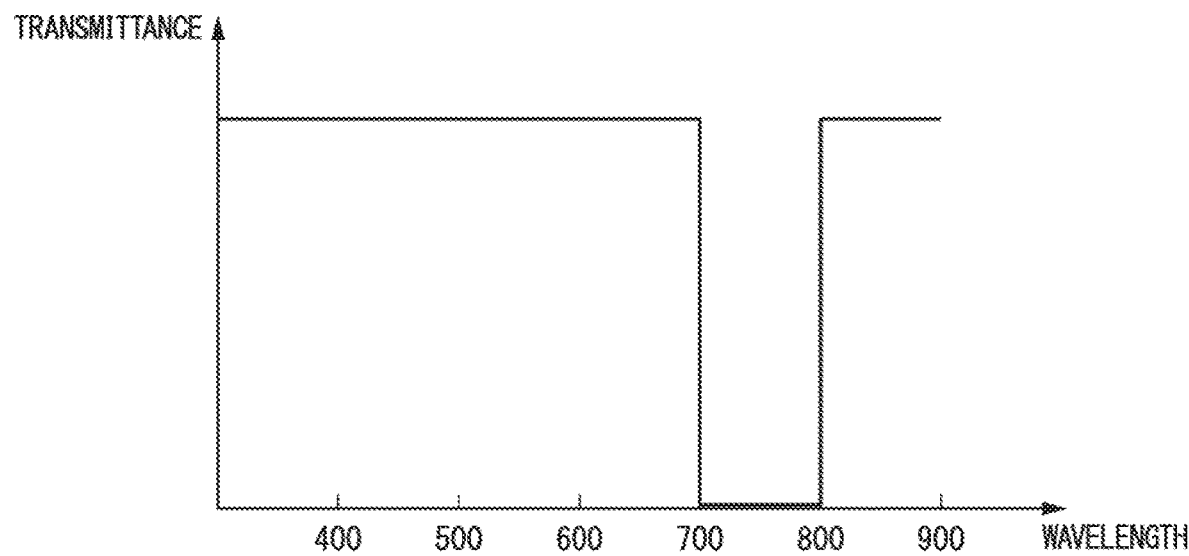
FIG. 2 is a graph showing characteristics of an excitation light cut filter of the first embodiment of the present invention.

FIG. 2 shows transmission characteristics of the excitation light cut filter 301a. The horizontal axis of the graph shown in FIG. 2 indicates wavelength, and the vertical axis indicates transmittance. The excitation light cut filter 301a filters out light in a wavelength band in which a wavelength is about 700 nm to about 800 nm. Further, the excitation light cut filter 301a transmits light in a wavelength band in which a wavelength is shorter than about 700 nm and light in a wavelength band in which a wavelength is equal to or longer than 800 nm. The wavelength band of light filtered out by the excitation light cut filter 301a includes a wavelength band of the excitation light. The wavelength band of the light transmitted by the excitation light cut filter 301a includes a wavelength band of the visible light and a wavelength band of the fluorescence.

The first light transmitted through the excitation light cut filter 301a is incident on the dichroic prism 302a. The dichroic prism 302a splits the first light transmitted through the excitation light cut filter 301a, that is, the first light from the subject 60 into the second light and the third light. The infrared light included in the second light incident on the dichroic prism 302a includes the fluorescence and does not include the excitation light. The second light incident on the dichroic prism 302a includes the fluorescence and the blue light. The dichroic prism 302a splits the third light into the red light and the green light.

Figure 3:
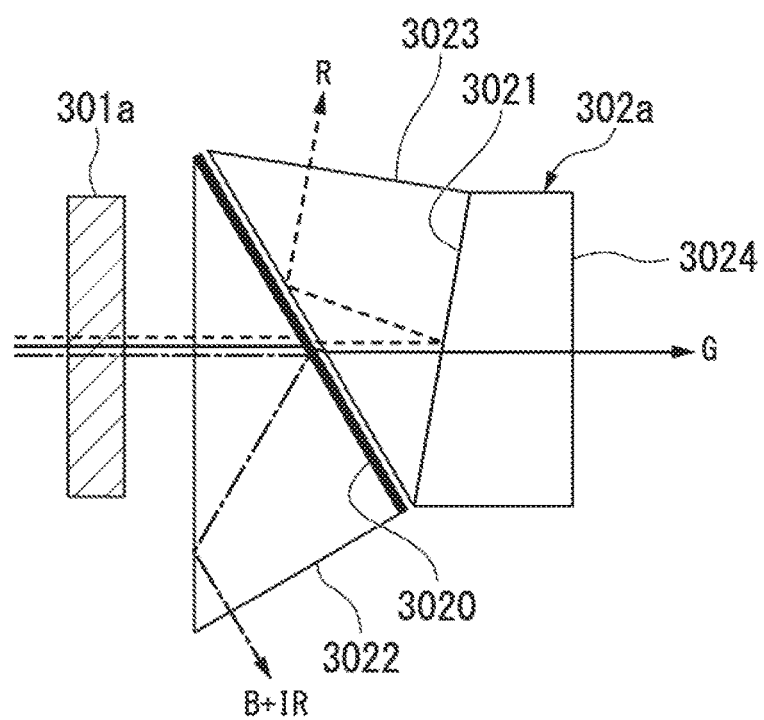
FIG. 3 is a schematic diagram showing a configuration of a dichroic prism of the first embodiment of the present invention.

FIG. 3 shows a configuration of the dichroic prism 302a. In FIG. 3, a schematic configuration of the excitation light cut filter 301a and the dichroic prism 302a is shown. The dichroic prism 302a includes a reflective surface 3020, a reflective surface 3021, an output surface 3022, an output surface 3023, and an output surface 3024. A thin film is formed on the reflective surface 3020 and the reflective surface 3021. The thin film transmits light with a specific wavelength and reflects light with other wavelengths rather than the specific wavelength. Therefore, the reflective surface 3020 and the reflective surface 3021 have a characteristic of light division.

Figure 4:
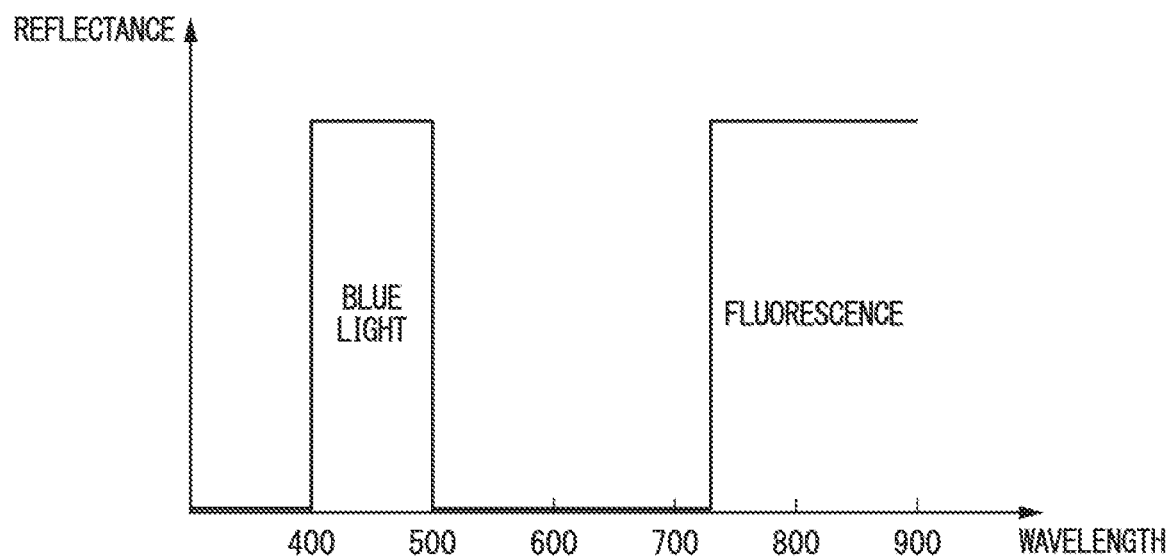
FIG. 4 is a graph showing characteristics of the dichroic prism of the first embodiment of the present invention.

The first light transmitted through the excitation light cut filter 301a is incident on the dichroic prism 302a. The first light incident on the dichroic prism 302a is incident on the reflective surface 3020. The reflective surface 3020 reflects the second light and transmits the third light. FIG. 4 shows reflection characteristics of the reflective surface 3020. The horizontal axis of the graph shown in FIG. 4 indicates wavelength, and the vertical axis indicates reflectance. The reflective surface 3020 reflects light in a wavelength band in which a wavelength is about 400 nm to about 500 nm and light in a wavelength band in which a wavelength is equal to or longer than about 730 nm. Further, the reflective surface 3020 transmits light in a wavelength band in which a wavelength is shorter than about 400 nm and light in a wavelength band in which a wavelength is about 500 nm to about 730 nm. The wavelength band of light reflected by the reflective surface 3020 includes a blue wavelength band and a fluorescence wavelength band. The wavelength band of the light transmitted by the reflective surface 3020 includes a green wavelength band and a red wavelength band.

The image sensor 304 and the image sensor 305a do not have a sensitivity to light having a wavelength shorter than 400 nm. Reflection characteristics of the reflective surface 3020 with respect to light in a wavelength band shorter than 400 nm may be an arbitrary. As shown in FIG. 2, the excitation light cut filter 301a can filter out light in the wavelength band in which a wavelength is about 700 nm to about 800 nm. Accordingly, reflection characteristics of the reflective surface 3020 with respect to light in a wavelength band of 700 nm to 800 nm may be arbitrary. The reflective surface 3020 may have a characteristic of reflecting light having a wavelength equal to or longer than a wavelength of a lower limit of a wavelength band that can be filtered out by the excitation light cut filter 301*a*. The wavelength band that can be filtered out by the excitation light cut filter 301*a* includes wavelengths of the excitation light. The second light reflected by the reflective surface 3020 is emitted in a direction of the image sensor 303*a* from the output surface 3022.

Figure 5:
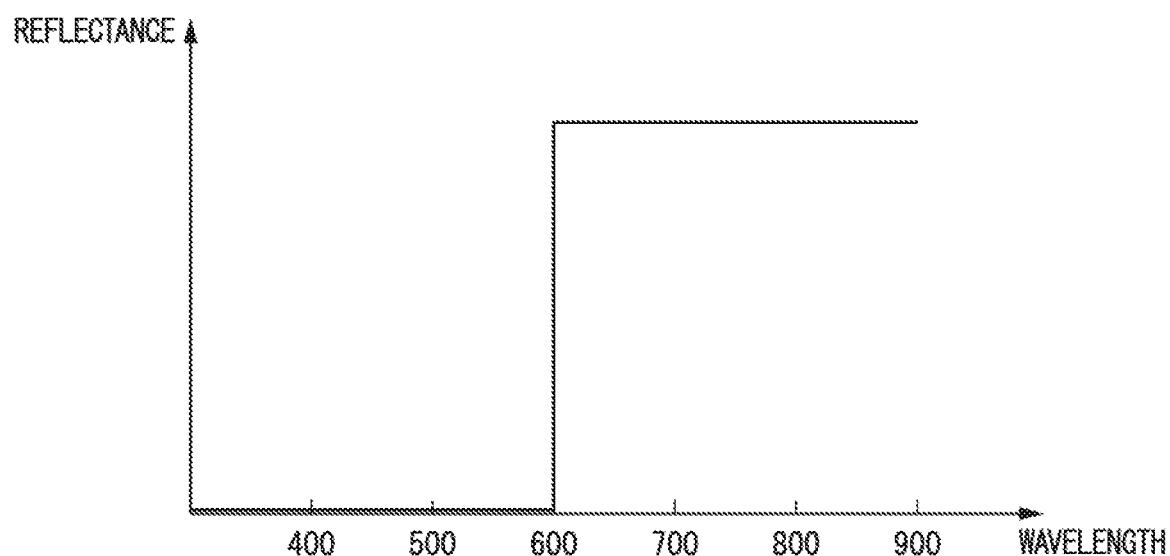
FIG. 5 is a graph showing characteristics of the dichroic prism of the first embodiment of the present invention.

The third light transmitted through the reflective surface 3020 is incident on the reflective surface 3021. The reflective surface 3021 reflects the red light and transmits the green light. FIG. 5 shows reflection characteristics of the reflective surface 3021. The horizontal axis of the graph shown in FIG. 5 indicates wavelength, and the vertical axis indicates reflectance. The reflective surface 3021 reflects light in a wavelength band in which a wavelength is equal to or longer than about 600 nm. Further, the reflective surface 3021 transmits light in a wavelength band in which a wavelength is shorter than about 600 nm. The wavelength band of the light reflected by the reflective surface 3021 includes a red wavelength band. The wavelength band of the light transmitted by the reflective surface 3021 includes a green wavelength band. The red light reflected by the reflective surface 3021 is output in the direction of the image sensor 304 from the output surface 3023. The green light transmitted through the reflective surface 3021 is output in a direction of the image sensor 305*a* from the output surface 3024.

The second light emitted from the output surface 3022 of the dichroic prism 302*a*, that is, the second light passing through the dichroic prism 302*a* is incident on the image sensor 303*a*. The image sensor 303*a* generates an IR signal according to the infrared light included in the second light and a B signal according to the blue light included in the second light. The infrared light included in the second light passing through the dichroic prism 302*a* includes the fluorescence and does not include the excitation light. Therefore, the image sensor 303*a* generates the IR signal according to the fluorescence included in the second light.

The red light emitted from the output surface 3023 of the dichroic prism 302*a*, that is, the red light passing through the dichroic prism 302*a* is incident on the image sensor 304. The image sensor 304 generates an R signal according to the red light. The green light emitted from the output surface 3024 of the dichroic prism 302*a*, that is, the green light passing through the dichroic prism 302*a* is incident on the image sensor 305*a*. The image sensor 305*a* generates a G signal according to the green light.

The arithmetic unit 40 generates the visible light image signal from the R signal, the G signal, and the B signal, and generates an infrared light image signal from the IR signal. The visible light image signal is a signal for displaying a visible light image. The infrared image signal is a signal for displaying an infrared image. Since the IR signal is according to a fluorescence component included in the infrared light, the infrared light image signal is a fluorescence image signal. The arithmetic unit 40 may perform image processing such as an interpolation process on at least one of the group consisting of the R signal, the G signal, the B signal, and the IR signal. For example, the arithmetic unit 40 is a processor.

The monitor 50 displays a visible light image according to the visible light image signal and a fluorescence image according to the fluorescence image signal. For example, the monitor 50 displays the visible light image and the fluorescence image that have been acquired at the same time, side by side. Alternatively, the monitor 50 superimposes and displays the visible light image and the fluorescence image that have been acquired at the same time.

Figure 6:
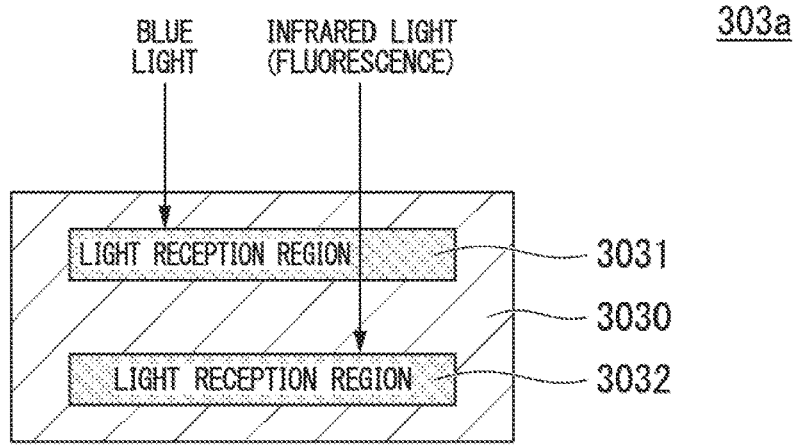
FIG. 6 is a cross-sectional view showing a configuration of an image sensor of the first embodiment of the present invention.

FIG. 6 shows a first example of a configuration of the image sensor 303*a*. In FIG. 6, a cross-section of the image sensor 303*a* is shown. As shown in FIG. 6, the image sensor 303*a* includes a semiconductor substrate 3030. The image sensor 303*a* includes a light reception region 3031 (a first light reception region) and a light reception region 3032 (a second light reception region). The light reception region 3031 and the light reception region 3032 are arranged in the semiconductor substrate 3030. The light reception region 3031 and the light reception region 3032 are stacked.

The second light passing through the dichroic prism 302*a* is incident on the light reception region 3031. The light reception region 3031 has a sensitivity to blue light. The light reception region 3031 generates a B signal according to the blue light. The infrared light transmitted through the light reception region 3031 is incident on the light reception region 3032. The light reception region 3032 has a sensitivity to infrared light. The light reception region 3032 generates an IR signal according to the infrared light. The infrared light included in the second light passing through the dichroic prism 302*a* includes the fluorescence and does not include the excitation light. Therefore, the fluorescence transmitted through the light reception region 3031 is incident on the light reception region 3032. The light reception region 3032 generates the IR signal according to the fluorescence.

The light reception region 3032 only has to have a sensitivity to light having a wavelength equal to or longer than a wavelength of a lower limit of a wavelength band that the excitation light cut filter 301*a* can filter out. The wavelength band that can be filtered out by the excitation light cut filter 301*a* includes wavelengths of the excitation light.

Figure 7:
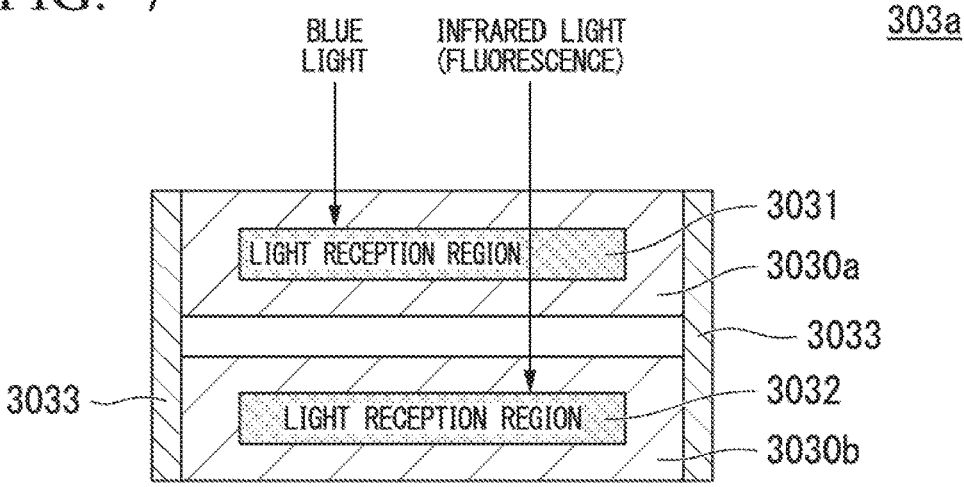
FIG. 7 is a cross-sectional view showing the configuration of the image sensor of the first embodiment of the present invention.

FIG. 7 shows a second example of a configuration of the image sensor 303*a*. In FIG. 7, a cross-section of the image sensor 303*a* is shown. As shown in FIG. 7, the image sensor 303*a* includes a semiconductor substrate 3030*a* (a first semiconductor substrate), a semiconductor substrate 3030*b* (a second semiconductor substrate), and a connection portion 3033. The image sensor 303*a* includes a light reception region 3031 (a first light reception region) and a light reception region 3032 (a second light reception region). The semiconductor substrate 3030*a* and the semiconductor substrate 3030*b* are stacked. The light reception region 3031 is arranged in the semiconductor substrate 3030*a*. The light reception region 3032 is arranged in the semiconductor substrate 3030*b*.

The semiconductor substrate 3030*a* and the semiconductor substrate 3030*b* are connected by the connection portion 3033. In FIG. 7, the connection portion 3033 is arranged at end portions of the semiconductor substrate 3030*a* and the semiconductor substrate 3030*b*. However, a position of the connection portion 3033 is not limited to the end portions of the semiconductor substrate 3030*a* and the semiconductor substrate 3030*b*.

The light reception region 3031 generates a B signal according to the blue light. The light reception region 3032 generates an IR signal according to the infrared light, that is, fluorescence.

Figure 8:
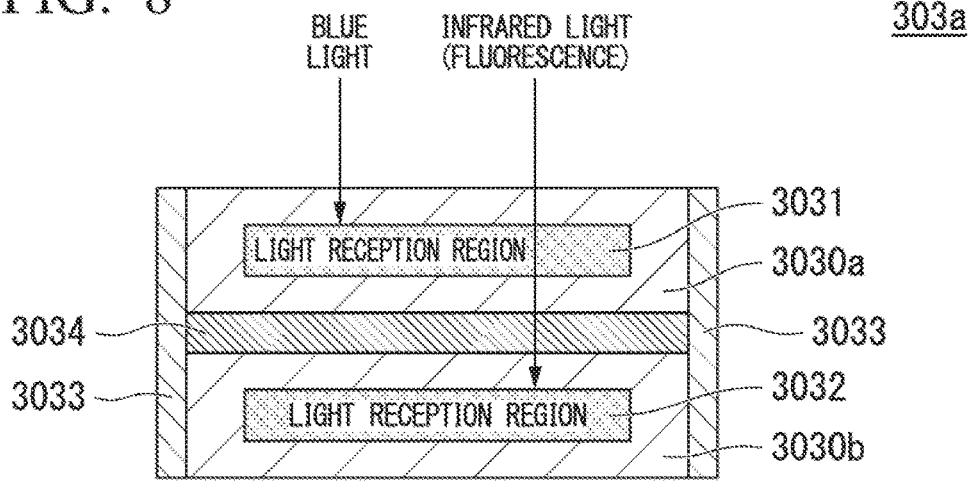
FIG. 8 is a cross-sectional view showing the configuration of the image sensor of the first embodiment of the present invention.

FIG. 8 shows a third example of the configuration of the image sensor 303*a*. In FIG. 8, a cross-section of the image sensor 303*a* is shown. As shown in FIG. 8, the image sensor 303*a* includes a semiconductor substrate 3030*a* (first semiconductor substrate), a semiconductor substrate 3030*b* (a second semiconductor substrate), and a connection portion 3033. The image sensor 303*a* includes a light reception region 3031 (a first light reception region) and a light reception region 3032 (a second light reception region). The light reception region 3031 is arranged in the semiconductor substrate 3030a. The light reception region 3032 is arranged in the semiconductor substrate 3030b. The image sensor 303a includes a blue light cut filter 3034. The blue light cut filter 3034 is arranged between the semiconductor substrate 3030a and the semiconductor substrate 3030b. The semiconductor substrate 3030a, the blue light cut filter 3034, and the semiconductor substrate 3030b are stacked.

The semiconductor substrate 3030a and the semiconductor substrate 3030b are connected by the connection portion 3033. In FIG. 8, the connection portion 3033 is arranged at end portions of the semiconductor substrate 3030a and the semiconductor substrate 3030b. However, a position of the connection portion 3033 is not limited to the end portions of the semiconductor substrate 3030a and the semiconductor substrate 3030b.

The light reception region 3031 generates a B signal according to the blue light. Fluorescent blue light and the blue light transmitted through the light reception region 3031 are incident on the blue light cut filter 3034. The blue light cut filter 3034 filters out the blue light and transmits the fluorescence. The fluorescence transmitted through the blue light cut filter 3034 is incident on the light reception region 3032. The light reception region 3032 generates an IR signal according to the fluorescence.

The blue light cut filter 3034 only has to have a characteristic of filtering out light in a blue wavelength band and transmitting light in a fluorescence wavelength band. The characteristics of the blue light cut filter 3034 with respect to a wavelength band other than the blue wavelength band and the fluorescence wavelength band are arbitrary.

The blue light is filtered out by the blue light cut filter 3034, and only the fluorescence is incident on the light reception region 3032. Therefore, the light reception region 3032 can detect only the fluorescence.

In FIGS. 6 to 8, the light reception region 3031 is arranged at a position closer to a subject in an optical path. For example, the semiconductor substrate 3030, the semiconductor substrate 3030a, and the semiconductor substrate 3030b are formed of silicon. An absorption rate in silicon with respect to light having a shorter wavelength is high. An absorption rate in silicon with respect to light having a longer wavelength is low. Therefore, light having a shorter wavelength is easily absorbed at a shallow position in the silicon. Light having a longer wavelength is easily absorbed at a deep position in the silicon.

Since these characteristics of silicon is used, the blue light having a shorter wavelength is detected by the light reception region 3031. The fluorescence having a longer wavelength is detected by the light reception region 3032. Since the blue wavelength band and the fluorescence wavelength band are separated, the blue light and the fluorescence are easily detected efficiently.

The light reception region 3031 shown in FIGS. 6 to 8 may detect a portion of the fluorescence included in the infrared light. The light reception region 3031 and the light reception region 3032 may detect the fluorescence. A signal according to the fluorescence and the blue light detected in the light reception region 3031 can eliminate an influence of the fluorescence. The second light incident on the light reception region 3031 includes the fluorescence and the blue light. The light reception region 3031 generates a B signal according to the fluorescence and the blue light. The arithmetic unit 40 generates the B signal only according to the blue light by removing a component derived from the fluorescence from the B signal generated in the light reception region 3031 according to a sensitivity of the light reception region 3031 to the fluorescence, a sensitivity of the light reception region 3032 to the fluorescence, and the IR signal generated in the light reception region 3032.

For example, a value Sig_B of the B signal generated by the light reception region 3031 is expressed using Equation (1). In Equation (1), S_b is a value of the signal according to the blue light. In Equation (1), S_ir is a value of a signal when all of the fluorescence incident on the image sensor 303a is detected in the light reception region 3031. In Equation (1), α indicates a proportion of absorption of the fluorescence in the light reception region 3031. That is, α indicates a sensitivity of the light reception region 3031 to the fluorescence.

$$Sig\_B = S\_b + \alpha \times S\_ir \quad (1)$$

For example, a value Sig_ir of the IR signal that is generated by the light reception region 3032 is expressed using Equation (2). In Equation (2), S_ir is a value of the signal when all of the fluorescence incident on the image sensor 303a is detected by the light reception region 3032. In Equation (2), β indicates a proportion of absorption of the fluorescence in the light reception region 3032. In other words, β indicates a sensitivity of the light reception region 3032 to the fluorescence.

$$Sig\_ir = \beta \times S\_ir \quad (2)$$

α and β can be calculated from a spectral sensitivity of the light reception region 3031 and the light reception region 3032 to fluorescence. α and β are parameters according to manufacturing conditions of the image sensor 303a. For example, the manufacturing conditions are a thickness in an optical axis direction of each of the light reception region 3031 and the light reception region 3032. Alternatively, a manufacturing condition is a gain of a reading circuit that reads signals generated in the light reception region 3031 and the light reception region 3032.

For example, when a bottom of the light reception region 3031 is located at a depth of 3 μm in the semiconductor substrate 3030 or the semiconductor substrate 3030a, all of the blue light incident on the light reception region 3031 is detected by the light reception region 3031. On the other hand, about 25% of the fluorescence incident on the light reception region 3031 is detected by the light reception region 3031. About 75% of the fluorescence incident on the light reception region 3031 is transmitted through the light reception region 3031. A proportion of the detection of the fluorescence in the light reception region 3032 is according to a position at which the light reception region 3032 is formed, a thickness of the light reception region 3032, or the like.

The arithmetic unit 40 can calculate a value α×S_ir of the signal according to the fluorescence detected by the light reception region 3031 by multiplying the value Sig_ir, that is, β×S_ir of the IR signal generated by the light reception region 3032 by a ratio, that is, α/β between α and β. The arithmetic unit 40 can calculate a value S_b of the signal according to the blue light detected by the light reception region 3031 by subtracting the value α×S_ir from the value Sig_B of the IR signal generated by the light reception region 3032. As a result, the arithmetic unit 40 can generate the B signal according to only the blue light.

In the first embodiment, the blue light and the infrared light, that is, the fluorescence are detected by the image sensor 303a. Thus, an optical element for splitting only the infrared light, that is, the fluorescence from other light is not necessary. As a result, it is possible to make the endoscope device 1a that is an imaging device a small size or lightweight.

An image sensor in which pixels that respectively detect the red light, the green light, and the blue light, and a pixel that detects the infrared light are arranged in the same imaging surface is conceivable. This image sensor can simultaneously acquire the visible light image and the infrared light image. However, since four types of pixel are arranged in the same imaging surface, resolution is low. As compared with this image sensor, the endoscope device 1a of the first embodiment can acquire a higher quality image.

(First Modification Example)

Figure 9:
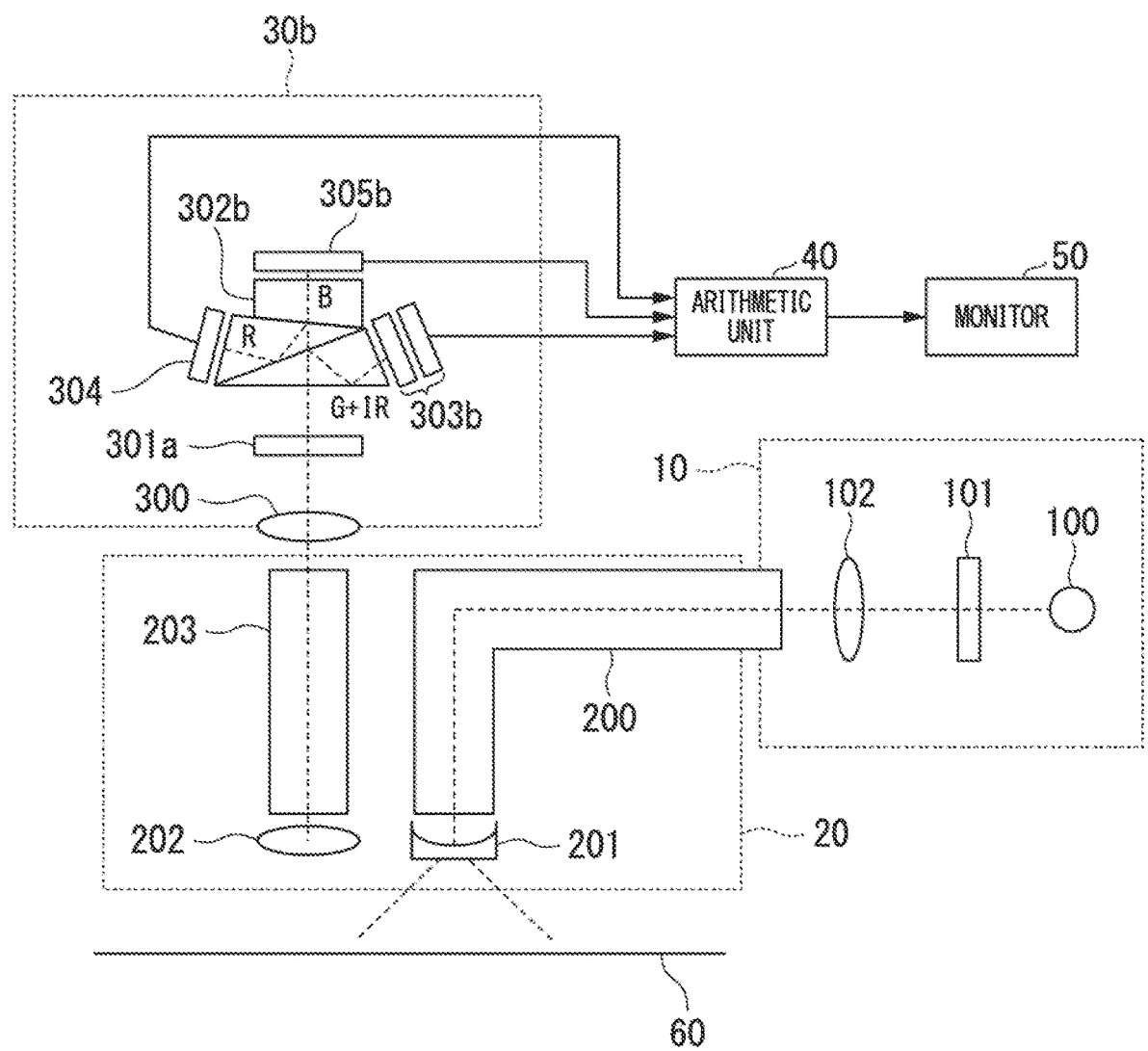
FIG. 9 is a block diagram showing a configuration of an endoscope device of a first modification example in the first embodiment of the present invention.

FIG. 9 shows a configuration of an endoscope device 1b of a first modification example of the first embodiment. As shown in FIG. 9, the endoscope device 1b includes a light source unit 10, an endoscope scope unit 20, a camera head 30b, an arithmetic unit 40, and a monitor 50. In FIG. 9, a schematic configuration of the light source unit 10, the endoscope scope unit 20, and the camera head 30b is shown.

Differences between the configuration shown in FIG. 9 and the configuration shown in FIG. 1 will be described.

The camera head 30b includes an image formation lens 300, an excitation light cut filter 301a, a dichroic prism 302b (a light splitting unit), an image sensor 303b (a first imaging unit), an image sensor 304 (a second imaging unit and a third imaging unit), and an image sensor 305b (a second imaging unit and a fourth imaging unit).

The first light transmitted through the excitation light cut filter 301a is incident on the dichroic prism 302b. The dichroic prism 302b splits the first light from the subject 60 into second light and third light. The second light includes infrared light and green light. The third light includes red light and blue light. The infrared light included in the second light incident on the dichroic prism 302b includes fluorescence and does not include excitation light. Thus, the second light incident on the dichroic prism 302b includes the fluorescence and the green light. The dichroic prism 302b splits the third light into red light and blue light.

The second light passing through the dichroic prism 302b is incident on the image sensor 303b. The image sensor 303b generates an IR signal according to the infrared light, that is, the fluorescence included in the second light, and a G signal according to the green light included in the second light. The configuration of the image sensor 303b is the same as the configuration of the image sensor 303a. The blue light passing through the dichroic prism 302b is incident on the image sensor 305b. The image sensor 305b generates a B signal according to the blue light.

Regarding other aspects, the configuration shown in FIG. 9 is the same as the configuration shown in FIG. 1.

(Second Modification Example)

Figure 10:
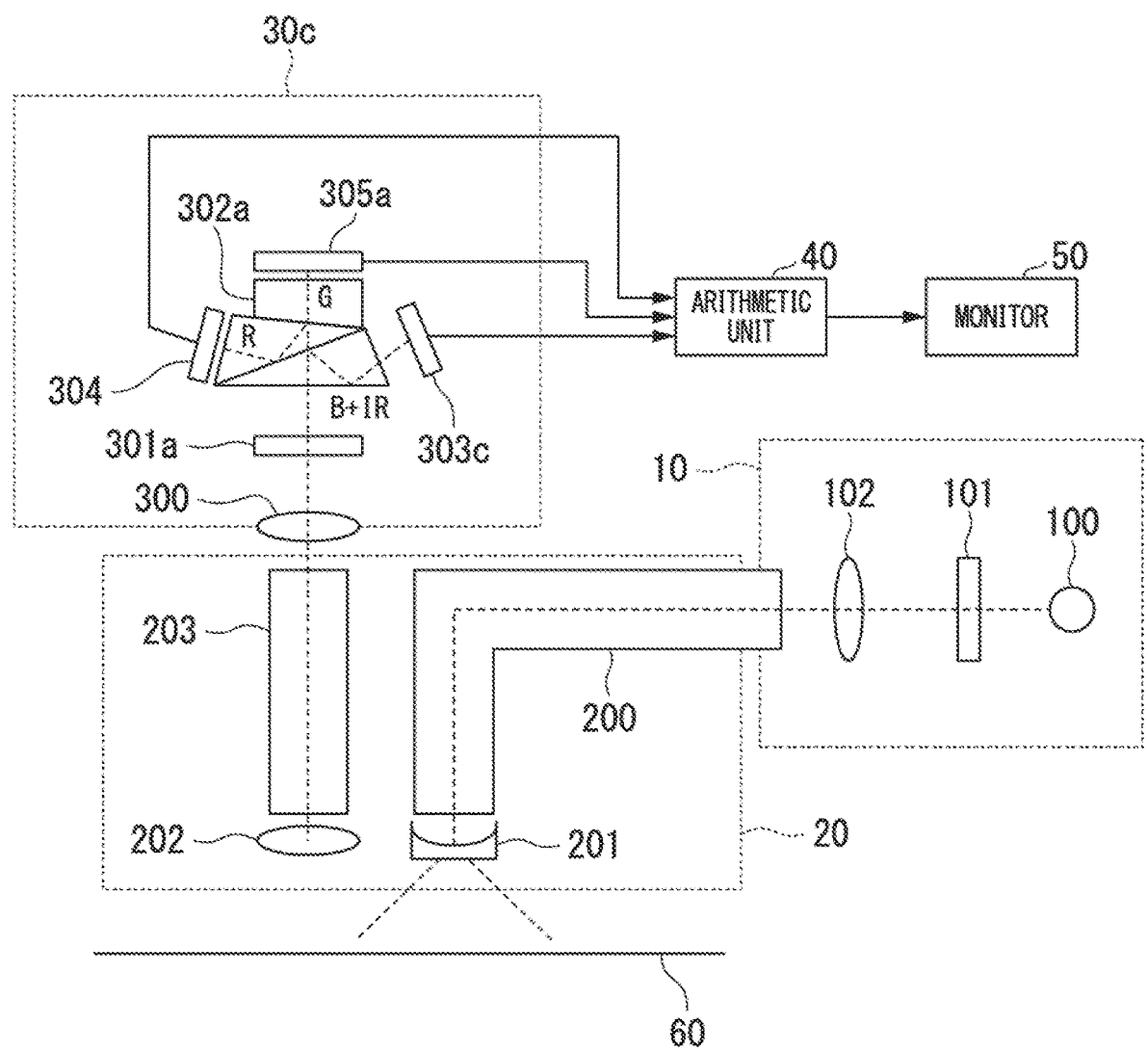
FIG. 10 is a block diagram showing a configuration of an endoscope device of a second modification example in the first embodiment of the present invention.

FIG. 10 shows a configuration of an endoscope device 1c of a second modification example of the first embodiment. As shown in FIG. 10, the endoscope device 1c includes a light source unit 10, an endoscope scope unit 20, a camera head 30c, an arithmetic unit 40, and a monitor 50. In FIG. 10, a schematic configuration of the light source unit 10, the endoscope scope unit 20, and the camera head 30c is shown.

Differences between the configuration shown in FIG. 10 and the configuration shown in FIG. 1 will be described.

The camera head 30c includes an image formation lens 300, an excitation light cut filter 301a, a dichroic prism 302b (a light splitting unit), an image sensor 303c (a first imaging unit), an image sensor 304 (a second imaging unit and a third imaging unit), and an image sensor 305a (a second imaging unit and a fourth imaging unit).

The second light passing through the dichroic prism 302a is incident on the image sensor 303c. The image sensor 303c generates an IR signal according to the infrared light, that is, the fluorescence included in the second light, and a B signal according to the blue light included in the second light.

FIG. 11 shows a pixel array of the image sensor 303c. The image sensor 303c includes a plurality of pixels 3035A and a plurality of pixels 3035b. The plurality of pixels 3035a and the plurality of pixels 3035b are arranged in a matrix form. Filters that transmit the blue light are arranged on surfaces of the plurality of pixels 3035a. Filters that transmit the infrared light, that is, the fluorescence are arranged on surfaces of the plurality of pixels 3035b. The plurality of pixels 3035a generate a B signal according to the blue light. The plurality of pixels 3035b generate an IR signal according to the infrared light, that is, the fluorescence.

One pixel of the image sensor 304 and one pixel of the image sensor 305a correspond to two pixels 3035a and two pixels 3035b. To match the numbers of pixels, the arithmetic unit 40 may add and average the B signals generated by the two pixels 3035a corresponding to one pixel of the image sensor 304 and one pixel of the image sensor 305a, decrease the number of pixels of the B signal to ½, and generate a visible light image signal from the R signal, the G signal, and the B signal.

Regarding other aspects, the configuration shown in FIG. 10 is the same as the configuration shown in FIG. 1.

The pixel size in the image sensor 303c may be smaller than a pixel size in the image sensor 304 and a pixel size in the image sensor 305a. For example, the pixel size in the image sensor 303c is ½ of the pixel size in the image sensor 304 and the pixel size in the image sensor 305a. The resolution of the visible light image and the fluorescence image acquired by the endoscope device 1c may be the same as a resolution of the visible light image and the fluorescence image acquired by the endoscope device 1a.

(Second Embodiment)

Figure 12:
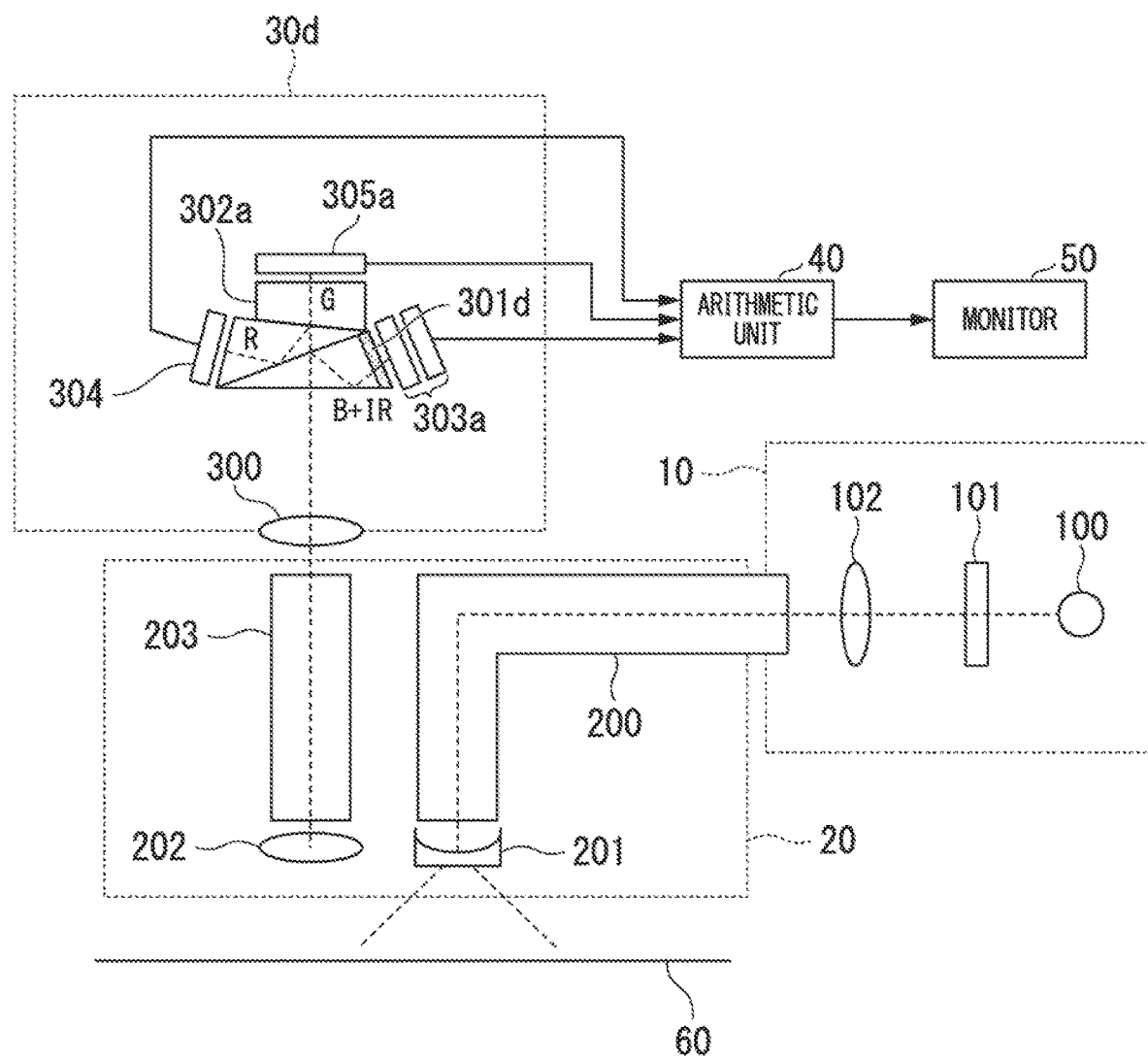
FIG. 12 is a block diagram showing a configuration of an endoscope device of a second embodiment of the present invention.

FIG. 12 shows a configuration of an endoscope device 1d of a second embodiment of the present invention. As shown in FIG. 12, the endoscope device 1d includes a light source unit 10, an endoscope scope unit 20, a camera head 30d, an arithmetic unit 40, and a monitor 50. In FIG. 12, a schematic configuration of the light source unit 10, the endoscope scope unit 20, and the camera head 30d is shown.

Differences between the configuration shown in FIG. 12 and the configuration shown in FIG. 1 will be described.

The camera head 30d includes an image formation lens 300, an excitation light cut filter 301d, a dichroic prism 302a (a light splitting unit), an image sensor 303a (a first imaging unit), an image sensor 304 (a second imaging unit and a third imaging unit), and an image sensor 305a (a second imaging unit and a fourth imaging unit).

As shown in FIG. 3, the dichroic prism 302a includes a surface, that is, an output surface 3022 that emits the second light. The excitation light cut filter 301d is arranged on the output surface 3022. The excitation light cut filter 301d comes in contact with the dichroic prism 302a. Transmission characteristics of the excitation light cut filter 301d are the same as the characteristics shown in FIG. 2.

The second light included in the first light from the subject 60 includes infrared light and blue light. The infrared light includes fluorescence and excitation light. A wavelength of the fluorescence is longer than a wavelength of the excitation light. The second light emitted from the output surface 3022 of the dichroic prism 302a, that is, the second light passing through the dichroic prism 302a is incident on the excitation light cut filter 301d. The excitation light cut filter 301d filters out the excitation light and transmits the fluorescence and the blue light. The excitation light cut filter 301d only has to be arranged on an optical path from the dichroic prism 302a to the image sensor 303a. The fluorescence and the blue light transmitted through the excitation light cut filter 301d are incident on the image sensor 303a.

Figure 13:
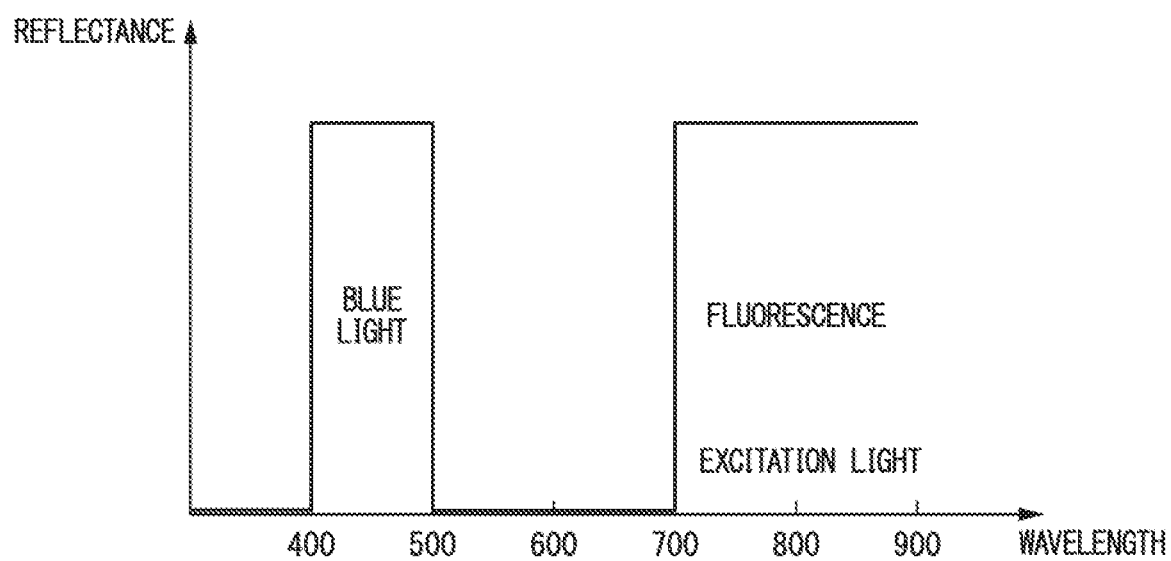
FIG. 13 is a graph showing characteristics of a dichroic prism in the second embodiment of the present invention.

Reflection characteristics of the reflective surface 3020 of the dichroic prism 302a differ from the reflection characteristics of the reflective surface 3020 in the first embodiment. The first light passing through the image formation lens 300 is incident on the dichroic prism 302a. The first light incident on the dichroic prism 302a is incident on the reflective surface 3020. The reflective surface 3020 reflects the second light and transmits the third light. FIG. 13 shows reflection characteristics of the reflective surface 3020. The horizontal axis of the graph shown in FIG. 13 indicates wavelength, and the vertical axis indicates reflectance. The reflective surface 3020 reflects light in a wavelength band in which a wavelength is about 400 nm to about 500 nm and light in a wavelength band in which a wavelength is equal to or longer than about 700 nm. Further, the reflective surface 3020 transmits light in a wavelength band in which a wavelength is shorter than about 400 nm and light in a wavelength band in which a wavelength is about 500 nm to about 700 nm. The wavelength band of light reflected by the reflective surface 3020 includes a blue wavelength band, an excitation light wavelength band, and a fluorescence wavelength band. The wavelength band of the light transmitted by the reflective surface 3020 includes a green wavelength band and a red wavelength band.

The image sensor 304 and the image sensor 305a do not have a sensitivity to light having a wavelength shorter than 400 nm. Therefore, reflection characteristics of the reflective surface 3020 with respect to light in a wavelength band shorter than 400 nm are arbitrary. Since the infrared light is not incident on the image sensor 304, the reflective surface 3020 reflects the light in the wavelength band in which a wavelength is equal to or longer than about 700 nm. Further, as shown in FIG. 2, the excitation light cut filter 301d can filter out light in the wavelength band in which a wavelength is about 700 nm to about 800 nm. The wavelength band that can be filtered out by the excitation light cut filter 301d includes wavelengths of the excitation light.

Regarding other aspects, the configuration shown in FIG. 12 is the same as the configuration shown in FIG. 1. In the endoscope device 1b shown in FIG. 9, an excitation light cut filter that filters out the excitation light and transmits the fluorescence and the green light may be arranged at the same position as that of the excitation light cut filter 301d.

In the second embodiment, the blue light and the infrared light, that is, the fluorescence are detected by the image sensor 303a. Thus, an optical element for splitting only the infrared light, that is, the fluorescence from other light is not necessary. As a result, it is possible to achieve a small size or light weight of the endoscope device 1d that is an imaging device.

Further, since the excitation light cut filter 301d is arranged on the output surface 3022 of the dichroic prism 302a, a space in which the excitation light cut filter 301d is arranged can be saved.

(Third Embodiment)

Figure 14:
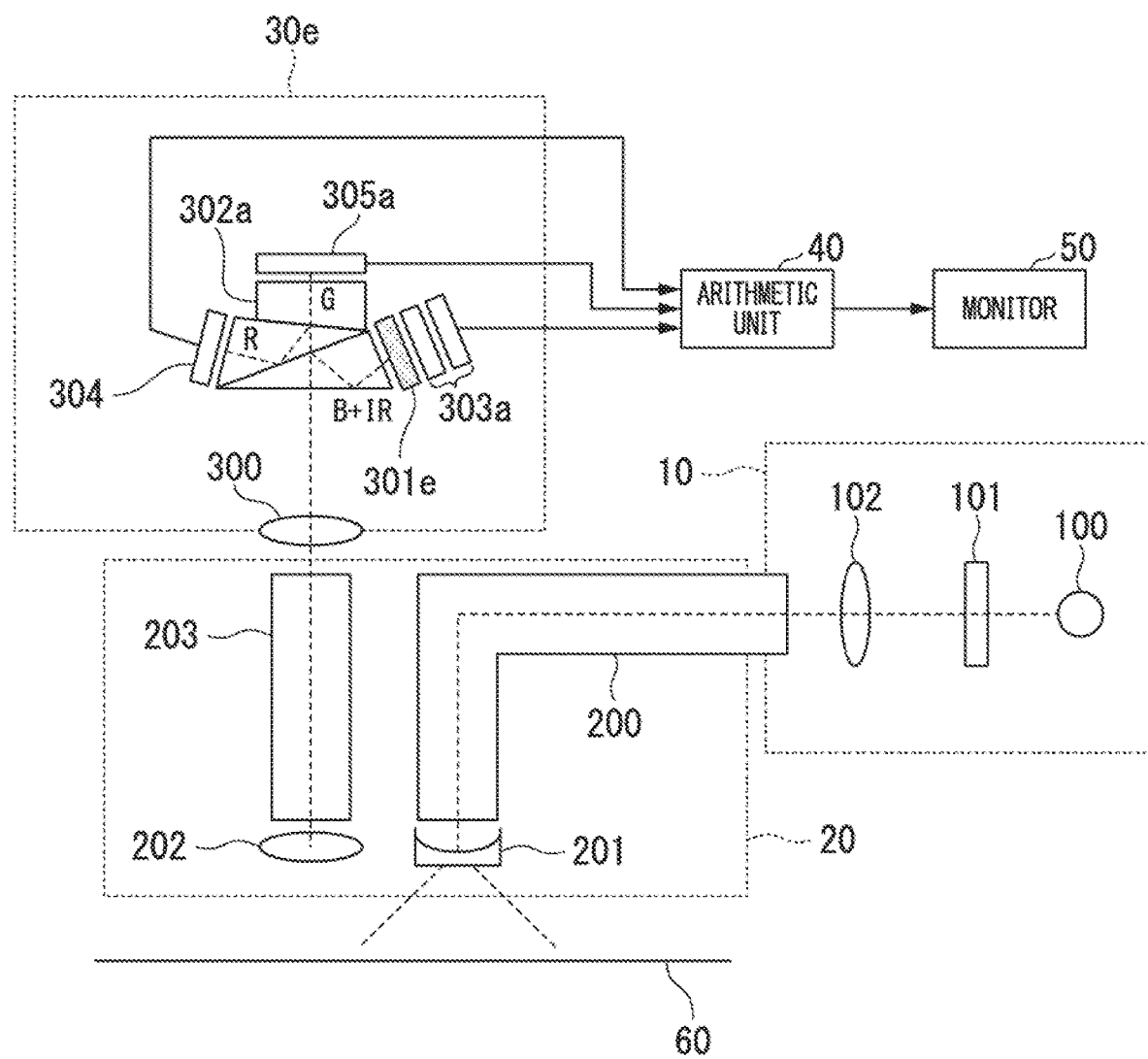
FIG. 14 is a block diagram showing a configuration of an endoscope device of a third embodiment of the present invention.

FIG. 14 shows a configuration of an endoscope device 1e of a third embodiment of the present invention. As shown in FIG. 14, the endoscope device 1e includes a light source unit 10, an endoscope scope unit 20, a camera head 30e, an arithmetic unit 40, and a monitor 50. In FIG. 14, a schematic configuration of the light source unit 10, the endoscope scope unit 20, and the camera head 30e is shown.

Differences between the configuration shown in FIG. 14 and the configuration shown in FIG. 1 will be described.

The camera head 30e includes an image formation lens 300, an excitation light cut filter 301e, a dichroic prism 302a (a light splitting unit), an image sensor 303a (a first imaging unit), an image sensor 304 (a second imaging unit and a third imaging unit), and an image sensor 305a (a second imaging unit and a fourth imaging unit).

The excitation light cut filter 301e is arranged on a surface of the light reception region 3031 of the image sensor 303a. The excitation light cut filter 301e and the image sensor 303a come in contact with each other. The excitation light cut filter 301e includes an organic material. The organic material filters out the excitation light and transmits at least one of the group consisting of the green light and the blue light, and the fluorescence. In the endoscope device 1e shown in FIG. 14, the organic material filters out the excitation light, and transmits the blue light and the fluorescence. For example, the excitation light cut filter 301e is a color filter arranged on a surface of the light reception region 3031 of the image sensor 303a. The excitation light cut filter 301e may be a filter formed of an optical multilayer film arranged on the surface of the light reception region 3031 of the image sensor 303a. The optical multilayer film includes a dielectric thin film formed of one or more layers having a high refractive index, and a dielectric thin film formed of one or more layers having a low refractive index. The dielectric thin film having a high refractive index and the dielectric thin film having a low refractive index are alternately stacked.

The second light included in the first light from the subject 60 includes infrared light and blue light. The infrared light includes fluorescence and excitation light. A wavelength of the fluorescence is longer than a wavelength of the excitation light. The second light emitted from the output surface 3022 of the dichroic prism 302a, that is, the second light passing through the dichroic prism 302a is incident on the excitation light cut filter 301e. The excitation light cut filter 301e filters out the excitation light and transmits the fluorescence and the blue light. The excitation light cut filter 301e only has to be arranged on an optical path from the dichroic prism 302a to the image sensor 303a. The fluorescence and the blue light transmitted through the excitation light cut filter 301e are incident on the image sensor 303a.

Figure 15:
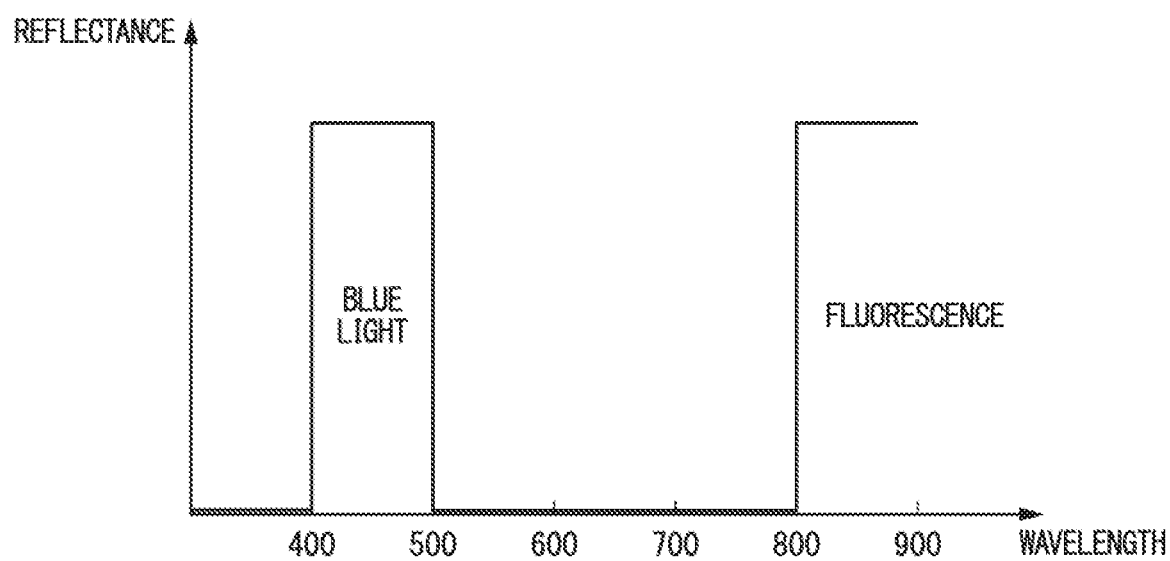
FIG. 15 is a graph showing characteristics of an excitation light cut filter of the third embodiment of the present invention.

FIG. 15 shows transmission characteristics of the excitation light cut filter 301e. A horizontal axis of a graph shown in FIG. 15 indicates wavelength, and a vertical axis indicates transmittance. The excitation light cut filter 301e filters out light in a wavelength band in which a wavelength is shorter than about 400 nm and light in a wavelength band in which a wavelength is about 500 nm to about 800 nm. Further, the excitation light cut filter 301e transmits light in a wavelength band in which a wavelength is about 400 nm to about 500 nm, and light in a wavelength band in which a wavelength is equal to or longer than 800 nm. The wavelength band of light filtered out by the excitation light cut filter 301e includes a wavelength band of the excitation light. The wavelength band of the light transmitted by the excitation light cut filter 301e includes a wavelength band of the visible light and a wavelength band of the fluorescence. Transmission characteristics of the excitation light cut filter 301e with respect to the light in the wavelength band shorter than 400 nm are arbitrary. Further, transmission characteristics of the excitation light cut filter 301e with respect to the light in the wavelength band of 500 nm to 800 nm are arbitrary.

Regarding other aspects, the configuration shown in FIG. 14 is the same as the configuration shown in FIG. 1. In the endoscope device 1*b* shown in FIG. 9, an excitation light cut filter that filters out the excitation light and transmits the fluorescence and the green light may be arranged at the same position as that of the excitation light cut filter 301*e*.

In the third embodiment, the blue light and the infrared light, that is, the fluorescence are detected by the image sensor 303*a*. Thus, an optical element for splitting only the infrared light, that is, the fluorescence from other light is not necessary. As a result, it is possible to achieve a small size or light weight of the endoscope device 1*e* that is an imaging device.

It is possible to realize the function of the excitation light cut filter 301*e* using a filter on the image sensor 303*a*.

(Fourth Embodiment)

Figure 16:
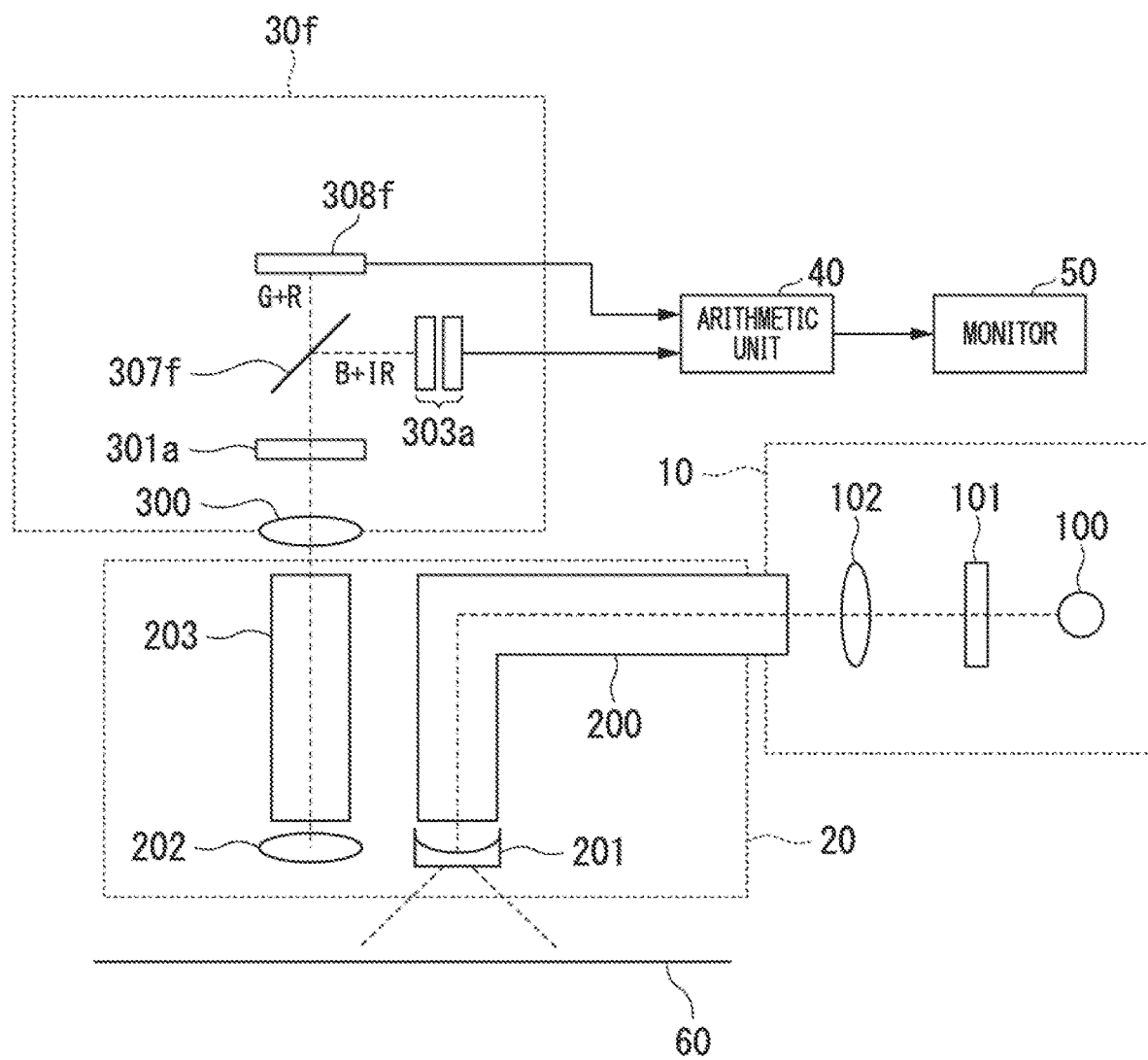
FIG. 16 is a block diagram showing a configuration of an endoscope device according to a fourth embodiment of the present invention.

FIG. 16 shows a configuration of an endoscope device 1*f* of a fourth embodiment of the present invention. As shown in FIG. 16, the endoscope device 1*f* includes a light source unit 10, an endoscope scope unit 20, a camera head 30*f*, an arithmetic unit 40, and a monitor 50. In FIG. 16, a schematic configuration of the light source unit 10, the endoscope scope unit 20, and the camera head 30*f* is shown.

Differences between the configuration shown in FIG. 16 and the configuration shown in FIG. 1 will be described.

The camera head 30*f* includes an image formation lens 300, an excitation light cut filter 301*a*, an image sensor 303*a* (a first imaging unit), a dichroic mirror 307*f* (a light splitting unit), and an image sensor 308*f* (a second imaging unit).

The first light transmitted through the excitation light cut filter 301*a* is incident on the dichroic mirror 307*f*. The dichroic mirror 307*f* splits the first light from the subject 60 into second light and third light. The second light includes infrared light and blue light. The third light includes red light and green light. The infrared light included in the second light incident on the dichroic mirror 307*f* includes fluorescence and does not include excitation light. Thus, the second light incident on the dichroic mirror 307*f* includes the fluorescence and the blue light.

The dichroic mirror 307*f* reflects the second light and transmits the third light. The second light reflected by the dichroic mirror 307*f* is incident on the image sensor 303*a*. The third light transmitted through the dichroic mirror 307*f* is incident on the image sensor 308*f*. The image sensor 308*f* generates an R signal according to the red light included in the third light, and a G signal according to the green light included in the third light. For example, in the image sensor 308*f*, a pixel that detects the red light and a pixel that detects the green light are arranged on the same imaging surface.

Regarding other aspects, the configuration shown in FIG. 16 is the same as the configuration shown in FIG. 1. In the endoscope device 1*f* shown in FIG. 16, an excitation light cut filter that filters out the excitation light and transmits the fluorescence and the blue light may be arranged at the same position as that of the excitation light cut filter 301*e*.

In the fourth embodiment, the blue light and the infrared light, that is, the fluorescence are detected by the image sensor 303*a*. Thus, an optical element for splitting only the infrared light, that is, the fluorescence from other light is not necessary. As a result, it is possible to achieve a small size or light weight of the endoscope device 1*f* that is an imaging device.

(Fifth Embodiment)

Figure 17:
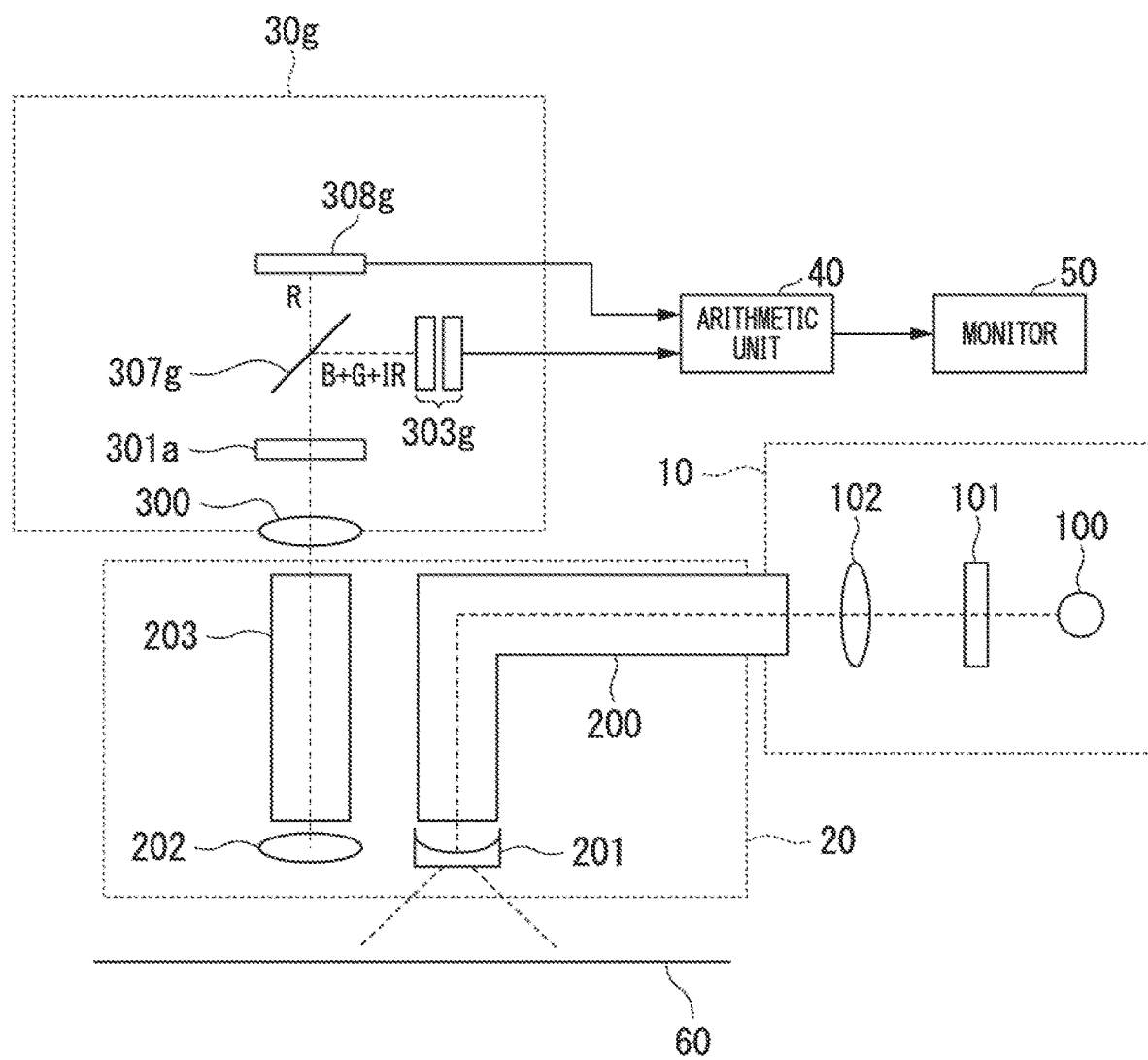
FIG. 17 is a block diagram showing a configuration of an endoscope device of a fifth embodiment of the present invention.

FIG. 17 shows a configuration of an endoscope device 1*g* of a fifth embodiment of the present invention. As shown in FIG. 17, the endoscope device 1*g* includes a light source unit 10, an endoscope scope unit 20, a camera head 30*g*, an arithmetic unit 40, and a monitor 50. In FIG. 17, a schematic configuration of the light source unit 10, the endoscope scope unit 20, and the camera head 30*g* is shown.

Differences between the configuration shown in FIG. 17 and the configuration shown in FIG. 1 will be described.

The camera head 30*g* includes an image formation lens 300, an excitation light cut filter 301*a*, an image sensor 303*g* (a first imaging unit), a dichroic mirror 307*g* (a light splitting unit), and an image sensor 308*g* (a second imaging unit).

The first light transmitted through the excitation light cut filter 301*a* is incident on the dichroic mirror 307*g*. The dichroic mirror 307*g* splits the first light from the subject 60 into second light and third light. The second light includes infrared light, blue light, and green light. The third light includes red light. The infrared light included in the second light incident on the dichroic mirror 307*g* includes fluorescence and does not include excitation light. Thus, the second light incident on the dichroic mirror 307*g* includes the fluorescence, the blue light, and the green light.

The dichroic mirror 307*g* reflects the second light and transmits the third light. The second light reflected by the dichroic mirror 307*g* is incident on the image sensor 303*g*. The image sensor 303*g* generates an IR signal according to the infrared light, that is, fluorescence included in the second light, a B signal according to the blue light included in the second light, and a G signal according to the green light included in the second light. The third light transmitted through the dichroic mirror 307*g* is incident on the image sensor 308*g*. The image sensor 308*g* generates the R signal according to the red light included in the third light.

Figure 18:
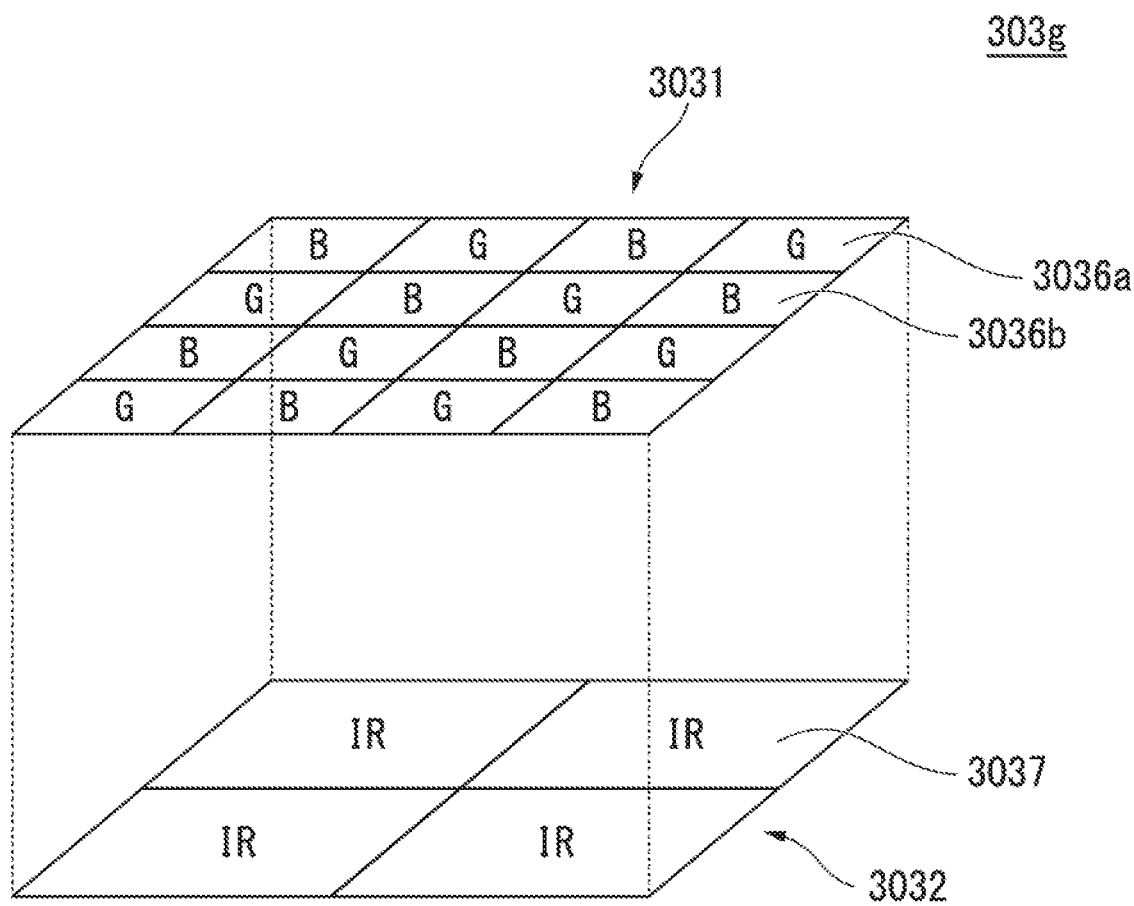
FIG. 18 is a reference diagram showing a pixel array of an image sensor of the fifth embodiment of the present invention.
Figure 19:
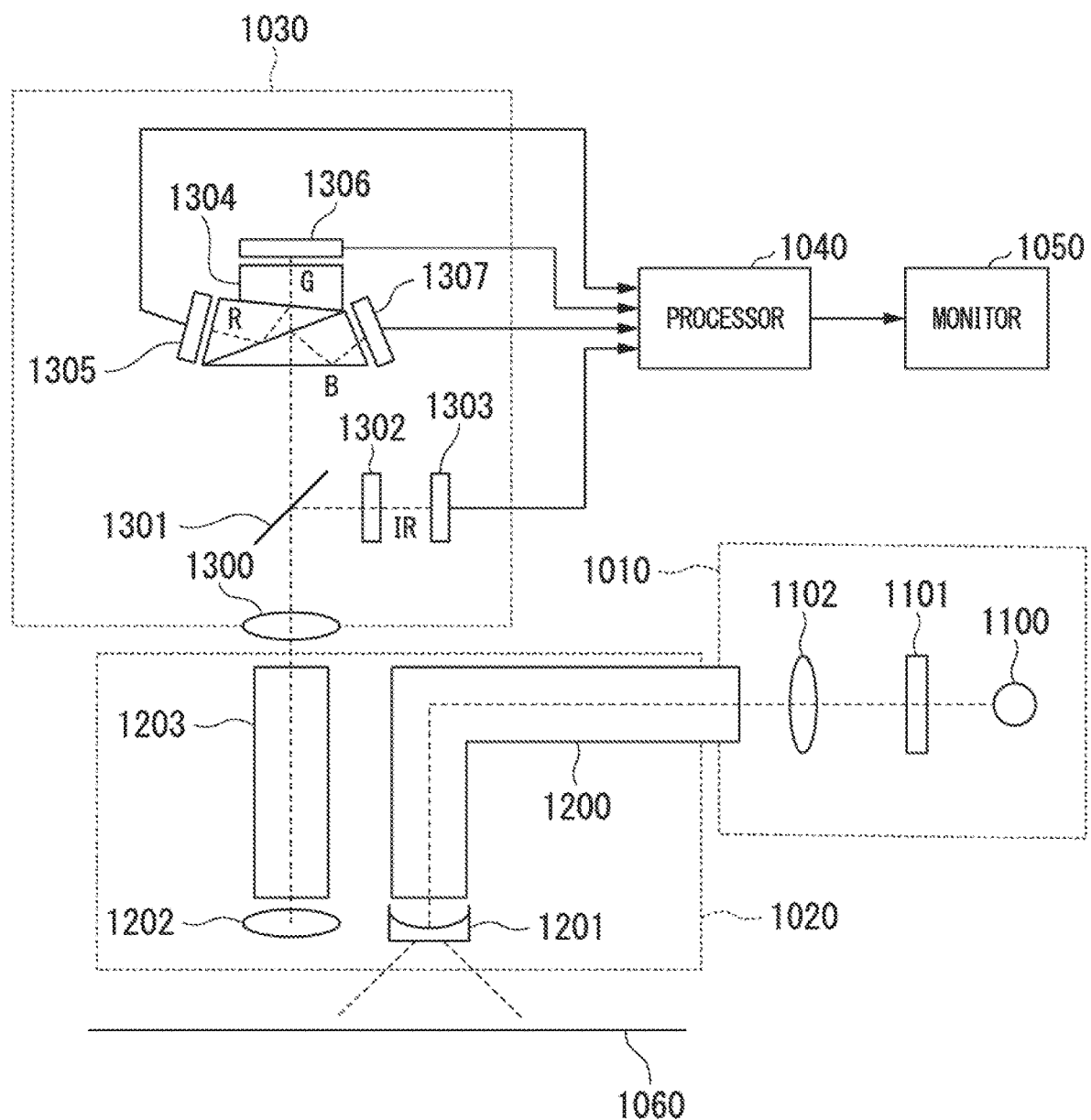
FIG. 19 is a block diagram showing a configuration of an endoscope device of the related art.

FIG. 18 shows a pixel array of an image sensor 303*g*. The image sensor 303*g* includes a light reception region 3031 and a light reception region 3032. The light reception region 3031 and the light reception region 3032 are stacked. The light reception region 3031 includes a plurality of pixels 3036*a* and a plurality of pixels 3036*b*. The plurality of pixels 3036*a* and the plurality of pixels 3036*b* are arranged in a matrix form. Filters that transmit the green light and the infrared light, that is, the fluorescence are arranged on surfaces of the plurality of pixels 3036*a*. Filters that transmit the blue light and the infrared light, that is, the fluorescence are arranged on surfaces of the plurality of pixels 3036*b*. The plurality of pixels 3036*a* generate a G signal according to the green light. The plurality of pixels 3036*b* generates a B signal according to the blue light.

The light reception region 3032 includes a plurality of pixels 3037. The plurality of pixels 3037 are arranged in a matrix form. The infrared light, that is, the fluorescence transmitted through the light reception region 3031 is incident on the light reception region 3032. The plurality of pixels 3037 generate an IR signal according to the infrared light, that is, the fluorescence.

Regarding other aspects, the configuration shown in FIG. 17 is the same as the configuration shown in FIG. 1. In the endoscope device 1*g* shown in FIG. 17, an excitation light cut filter that filters out the excitation light and transmits the fluorescence, the blue light, and the green light may be arranged at the same position as that of the excitation light cut filter 301*e*.

In the fifth embodiment, the blue light and the infrared light, that is, the fluorescence are detected by the image sensor 303*g*. Thus, an optical element for splitting only the infrared light, that is, the fluorescence from other light is not necessary. As a result, it is possible to achieve a small size or light weight of the endoscope device 1*g* that is an imaging device.

(Supplement)

The imaging device of each aspect of the present invention may not have a configuration corresponding to at least one of the group consisting of the light source unit 10, the endoscope scope unit 20, the image formation lens 300, the excitation light cut filter 301a, the excitation light cut filter 301d, the excitation light cut filter 301e, and the monitor 50.

The imaging device includes a light splitting unit, a first imaging unit, a second imaging unit, and an arithmetic unit. The imaging device corresponds to an endoscope device 1a, an endoscope device 1b, an endoscope device 1c, an endoscope device 1d, an endoscope device 1e, an endoscope device 1f, and an endoscope device 1g. The light splitting unit corresponds to a dichroic prism 302a, a dichroic prism 302b, a dichroic mirror 307f, and a dichroic mirror 307g. The first imaging unit corresponds to an image sensor 303a, an image sensor 303b, an image sensor 303c, and an image sensor 303g. The second imaging unit corresponds to an image sensor 304, an image sensor 305a, an image sensor 305b, an image sensor 308f, and an image sensor 308g. The arithmetic unit corresponds to an arithmetic unit 40.

The light splitting unit splits first light from a subject into second light and third light. The first light includes the second light and the third light. The second light includes infrared light, and at least one of the group consisting of green light and blue light. The third light includes red light. As shown in FIGS. 1, 10, 12, 14, and 16, when the second light includes the blue light and does not include the green light, the third light further includes the green light. As shown in FIG. 9, when the second light includes the green light and does not include the blue light, the third light further includes the blue light. A wavelength of the infrared light is longer than a wavelength of the red light. The wavelength of the red light is longer than a wavelength of the green light. The wavelength of the green light is longer than a wavelength of the blue light.

The first imaging unit includes a first light reception region and a second light reception region. The first light reception region corresponds to the light reception region 3031. The second light reception region corresponds to the light reception region 3032. Second light passing through the light splitting unit is incident on the first light reception region. The first light reception region generates at least one of the group consisting of a B signal according to the blue light and a G signal according to the green light. The infrared light transmitted through the first light reception region is incident on the second light reception region. The second light reception region generates an IR signal according to the infrared light.

The second imaging unit generates an R signal according to the red light included in the third light passing through the light splitting unit. As shown in FIGS. 1, 10, 12, 14, and 16, when the third light passing through the light splitting unit includes the green light and does not include the blue light, the second imaging unit may generate the G signal according to the green light. As shown in FIG. 9, when the third light passing through the light splitting unit includes the blue light and does not include the green light, the second imaging unit generates the B signal according to the blue light.

The arithmetic unit generates the visible light image signal from the R signal, the G signal, and the B signal, and generates the infrared light image signal from the IR signal.

The second light passing through the light splitting unit includes the infrared light. As shown in FIGS. 1, 9, 10, 12, and 14, the second light passing through the light splitting unit includes any one of the blue light and the green light. As shown in FIGS. 1, 10, 12, and 14, when the third light includes the green light, the light splitting unit splits the third light into red light and green light. As shown in FIG. 9, when the third light includes the blue light, the light splitting unit further splits the third light into the red light and the blue light. The second imaging unit includes a third imaging unit and a fourth imaging unit. The third imaging unit corresponds to the image sensor 304. The fourth imaging unit corresponds to the image sensor 305a and the image sensor 305b. The third imaging unit generates an R signal according to the red light passing through the light splitting unit. As shown in FIGS. 1, 10, 12, and 14, when the third light includes the green light, the fourth imaging unit generates a G signal according to the green light passing through the light splitting unit. As shown in FIG. 9, when the third light includes the blue light, the fourth imaging unit generates a B signal according to the blue light passing through the light splitting unit.

An excitation light cut filter may be arranged on an optical path from the subject to the light splitting unit. The excitation light cut filter corresponds to the excitation light cut filter 301a. The infrared light included in the second light in the first light from the subject includes excitation light and fluorescence. A wavelength of the fluorescence is longer than a wavelength of the excitation light. The first light from the subject is incident on the excitation light cut filter. The excitation light cut filter filters out the excitation light, and transmits the red light, the green light, the blue light, and the fluorescence. In this case, the second light included in the first light passing through the excitation light cut filter includes the fluorescence, and at least one of the group consisting of the green light and the blue light. The third light included in the first light passing through the excitation light cut filter is the same as the above third light.

The excitation light cut filter may be arranged on an optical path from the light splitting unit to the first imaging unit. The excitation light cut filter corresponds to the excitation light cut filter 301d and the excitation light cut filter 301e. The second light passing through the light splitting unit is incident on the excitation light cut filter. The excitation light cut filter filters out the excitation light, and transmits the fluorescence and at least one of the group consisting of the green light and the blue light. In this case, the second light passing through the excitation light cut filter includes the fluorescence and at least one of the group consisting of the green light and the blue light. The third light passing through the light splitting unit is the same as the above third light.

In the imaging device, at least one of the group consisting of the blue light and the green light, and the infrared light are detected by the first imaging unit. Therefore, an optical element for splitting only the infrared light from other light is not necessary. As a result, it is possible to make the imaging device a small size or lightweight.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:

1. An imaging device, comprising:
   a light splitting unit configured to split first light from a subject into second light and third light, the first light including the second light and the third light, the second light including infrared light and at least one of a group consisting of green light and blue light, the third light including red light, the third light further including the green light when the second light includes the blue light and does not include the green light, the third light further including the blue light when the second light includes the green light and does not include the blue light, a wavelength of the infrared light being longer than a wavelength of the red light, the wavelength of the red light being longer than a wavelength of the green light, and the wavelength of the green light being longer than a wavelength of the blue light;

a first imaging unit which includes a first light reception region and a second light reception region, the second light passing through the light splitting unit being incident on the first light reception region, the first light reception region configured to generate at least one of the group consisting of a B signal according to the blue light and a G signal according to the green light, the infrared light transmitted through the first light reception region being incident on the second light reception region, and the second light reception region configured to generate an IR signal according to the infrared light;

a second imaging unit configured to generate an R signal according to the red light included in the third light passing through the light splitting unit, generate the G signal when the third light passing through the light splitting unit includes the green light and does not include the blue light, and generate the B signal when the third light passing through the light splitting unit includes the blue light and does not include the green light;

an arithmetic unit configured to generate a visible light image signal from the R signal, the G signal, and the B signal and generate an infrared light image signal from the IR signal; and an excitation light cut filter arranged on an optical path from the subject to the light splitting unit, wherein the infrared light included in the second light in the first light from the subject includes excitation light and fluorescence, a wavelength of the fluorescence being longer than a wavelength of the excitation light, wherein the first light from the subject is incident on the excitation light cut filter, wherein the excitation light cut filter filters out the excitation light, and transmits the fluorescence, the red light, the green light, and the blue light, wherein the light splitting unit splits the first light transmitted through the excitation light cut filter into the second light and the third light, and wherein the fluorescence transmitted through the first light reception region is incident on the second light reception region, and the second light reception region is configured to generate the IR signal according to the fluorescence.

2. The imaging device according to claim 1,
wherein the second light passing through the light splitting unit includes the infrared light and one of the blue light and the green light,
the light splitting unit further splits the third light into the red light and the green light when the third light includes the green light, and the light splitting unit further splits the third light into the red light and the blue light when the third light includes the blue light, and the second imaging unit includes
a third imaging unit configured to generate the R signal according to the red light passing through the light splitting unit; and
a fourth imaging unit configured to generate the G signal according to the green light passing through the light splitting unit when the third light includes the green light, and generates the B signal according to the blue light passing through the light splitting unit when the third light includes the blue light.

3. The imaging device according to claim 1,
wherein the second light reception region has a sensitivity to light which has a wavelength equal to or longer than a wavelength of a lower limit of a wavelength band that is capable of being filtered out by the excitation light cut filter.

4. The imaging device according to claim 1,
wherein the first imaging unit includes a semiconductor substrate,
wherein the first light reception region and the second light reception region are arranged on the semiconductor substrate, and
wherein the first light reception region and the second light reception region are stacked.

5. The imaging device according to claim 1,
wherein the second light included in the first light from the subject includes the infrared light and the blue light, and the third light included in the first light from the subject includes the red light and the green light,
wherein the first light reception region is configured to generate the B signal according to the blue light,
wherein the second imaging unit is configured to generate the R signal according to the red light and the G signal according to the green light, and
wherein the arithmetic unit generates the B signal only according to the blue light by removing a component derived from the fluorescence from the B signal generated in the first light reception region, according to a sensitivity of the first light reception region to the fluorescence, a sensitivity of the second light reception region to the fluorescence, and the IR signal generated in the second light reception region.

6. An imaging device, comprising:
a light splitting unit configured to split first light from a subject into second light and third light, the first light including the second light and the third light, the second light including infrared light and at least one of a group consisting of green light and blue light, the third light including red light, the third light further including the green light when the second light includes the blue light and does not include the green light, the third light further including the blue light when the second light includes the green light and does not includes the blue light, a wavelength of the infrared light being longer than a wavelength of the red light, the wavelength of the red light being longer than a wavelength of the green light, and the wavelength of the green light being longer than a wavelength of the blue light;

a first imaging unit which includes a first light reception region and a second light reception region, the second light passing through the light splitting unit being incident on the first light reception region, the first light reception region configured to generate at least one of the group consisting of a B signal according to the blue light and a G signal according to the green light, the infrared light transmitted through the first light reception region being incident on the second light reception region, and the second light reception region configured to generate an IR signal according to the infrared light;
a second imaging unit configured to generate an R signal according to the red light included in the third light passing through the light splitting unit, generate the G signal when the third light passing through the light splitting unit includes the green light and does not include the blue light, and generate the B signal when the third light passing through the light splitting unit includes the blue light and does not include the green light;
an arithmetic unit configured to generate a visible light image signal from the R signal, the G signal, and the B signal and generate an infrared light image signal from the IR signal; and
an excitation light cut filter arranged on an optical path from the light splitting unit to the first imaging unit,
wherein the infrared light included in the second light in the first light from the subject includes excitation light and fluorescence, a wavelength of the fluorescence being longer than a wavelength of the excitation light,
wherein the second light passing through the light splitting unit is incident on the excitation light cut filter,
wherein the excitation light cut filter filters out the excitation light, and transmits the fluorescence, and at least one of the group consisting of the green light and the blue light, and
wherein the fluorescence transmitted through the first light reception region is incident on the second light reception region, and the second light reception region is configured to generate the IR signal according to the fluorescence.

7. The imaging device according to claim 6, wherein the excitation light cut filter is arranged on a surface of the first light reception region of the first imaging unit.

8. The imaging device according to claim 6, wherein the excitation light cut filter include an organic material, and
wherein the organic material filters out the excitation light and transmits at least one of the group consisting of the green light and the blue light, and the fluorescence.

9. The imaging device according to claim 6, wherein the second light included in the first light from the subject includes the infrared light and the blue light, and the third light included in the first light from the subject includes the red light and the green light,
wherein the first light reception region is configured to generate the B signal according to the fluorescence and the blue light,
wherein the second imaging unit is configured to generate the R signal according to the red light and the G signal according to the green light, and
wherein the arithmetic unit generates the B signal only according to the blue light by removing a component derived from the fluorescence from the B signal generated in the first light reception region, according to a sensitivity of the first light reception region to the fluorescence, a sensitivity of the second light reception region to the fluorescence, and the IR signal generated in the second light reception region.

10. An imaging device, comprising:
a light splitting unit configured to split first light from a subject into second light and third light, the first light including the second light and the third light, the second light including infrared light and at least one of a group consisting of green light and blue light, the third light including red light, the third light further including the green light when the second light includes the blue light and does not include the green light, the third light further including the blue light when the second light includes the green light and does not includes the blue light, a wavelength of the infrared light being longer than a wavelength of the red light, the wavelength of the red light being longer than a wavelength of the green light, and the wavelength of the green light being longer than a wavelength of the blue light;
a first imaging unit which includes a first light reception region and a second light reception region, the second light passing through the light splitting unit being incident on the first light reception region, the first light reception region configured to generate at least one of the group consisting of a B signal according to the blue light and a G signal according to the green light, the infrared light transmitted through the first light reception region being incident on the second light reception region, and the second light reception region configured to generate an IR signal according to the infrared light;
a second imaging unit configured to generate an R signal according to the red light included in the third light passing through the light splitting unit, generate the G signal when the third light passing through the light splitting unit includes the green light and does not include the blue light, and generate the B signal when the third light passing through the light splitting unit includes the blue light and does not include the green light;
an arithmetic unit configured to generate a visible light image signal from the R signal, the G signal, and the B signal and generate an infrared light image signal from the IR signal; and
an excitation light cut filter arranged on an optical path from the subject to the light splitting unit,
wherein the first imaging unit includes a first semiconductor substrate and a second semiconductor substrate,
wherein the first semiconductor substrate and the second semiconductor substrate are stacked,
wherein the second light included in the first light from the subject includes the infrared light and the blue light, the infrared light includes excitation light and fluorescence, a wavelength of the fluorescence being longer than a wavelength of the excitation light, and the third light included in the first light from the subject includes the red light and the green light,
wherein the first light from the subject is incident on the excitation light cut filter,
wherein the excitation light cut filter filters out the excitation light, and transmits the fluorescence, the red light, the green light, and the blue light,
wherein the light splitting unit splits the first light transmitted through the excitation light cut filter into the second light and the third light, and
wherein the first imaging unit further includes a blue light cut filter,
wherein the blue light cut filter is arranged between the first semiconductor substrate and the second semiconductor substrate,
wherein the first semiconductor substrate, the blue light cut filter, and the second semiconductor substrate are stacked, wherein the first light reception region is configured to generate the B signal according to the blue light, the fluorescence and the blue light transmitted through the first light reception region are incident on the blue light cut filter, the blue light cut filter filters out the blue light and transmits the fluorescence, the fluorescence transmitted through the blue light cut filter is incident on the second light reception region, and the second light reception region generates the IR signal according to the fluorescence, and the second imaging unit is configured to generate the R signal according to the red light and the G signal according to the green light.

11. An imaging device, comprising:
a light splitting unit configured to split first light from a subject into second light and third light, the first light including the second light and the third light, the second light including infrared light and at least one of a group consisting of green light and blue light, the third light including red light, the third light further including the green light when the second light includes the blue light and does not include the green light, the third light further including the blue light when the second light includes the green light and does not includes the blue light, a wavelength of the infrared light being longer than a wavelength of the red light, the wavelength of the red light being longer than a wavelength of the green light, and the wavelength of the green light being longer than a wavelength of the blue light;
a first imaging unit which includes a first light reception region and a second light reception region, the second light passing through the light splitting unit being incident on the first light reception region, the first light reception region configured to generate at least one of the group consisting of a B signal according to the blue light and a G signal according to the green light, the infrared light transmitted through the first light reception region being incident on the second light reception region, and the second light reception region configured to generate an IR signal according to the infrared light;
a second imaging unit configured to generate an R signal according to the red light included in the third light passing through the light splitting unit, generate the G signal when the third light passing through the light splitting unit includes the green light and does not include the blue light, and generate the B signal when the third light passing through the light splitting unit includes the blue light and does not include the green light;

an arithmetic unit configured to generate a visible light image signal from the R signal, the G signal, and the B signal and generate an infrared light image signal from the IR signal; and an excitation light cut filter arranged on an optical path from the light splitting unit to the first imaging unit,
wherein the first imaging unit includes a first semiconductor substrate and a second semiconductor substrate,
wherein the first semiconductor substrate and the second semiconductor substrate are stacked,
wherein the second light included in the first light from the subject includes the infrared light and the blue light, the infrared light includes excitation light and fluorescence, a wavelength of the fluorescence is longer than a wavelength of the excitation light, and the third light included in the first light from the subject includes the red light and the green light,
wherein the second light passing through the light splitting unit is incident on the excitation light cut filter,
wherein the excitation light cut filter filters out the excitation light, and transmits the fluorescence and the blue light, and
wherein the first imaging unit further includes a blue light cut filter,
wherein the blue light cut filter is arranged between the first semiconductor substrate and the second semiconductor substrate,
wherein the first semiconductor substrate, the blue light cut filter, and the second semiconductor substrate are stacked,
wherein the first light reception region is configured to generate the B signal according to the blue light, the fluorescence and the blue light transmitted through the first light reception region are incident on the blue light cut filter, the blue light cut filter filters out the blue light and transmits the fluorescence, the fluorescence transmitted through the blue light cut filter is incident on the second light reception region, and the second light reception region generates the IR signal according to the fluorescence, and
wherein the second imaging unit is configured to generate the R signal according to the red light and the G signal according to the green light.

* * * * *